(12) United States Patent
Li et al.

(10) Patent No.: US 11,964,170 B2
(45) Date of Patent: Apr. 23, 2024

(54) STANDARDIZED ARTIFICIAL INTELLIGENCE AUTOMATIC RADIATION THERAPY PLANNING METHOD AND SYSTEM

(71) Applicant: BEIJING LINKING MEDICAL TECHNOLOGY CO., LTD, Beijing (CN)

(72) Inventors: Gui Li, Beijing (CN); Qiang Li, Beijing (CN); Weiyang Fan, Beijing (CN); Hua Zhang, Beijing (CN)

(73) Assignee: BEIJING LINKING MEDICAL TECHNOLOGY CO., LTD., Beijing (CN)

( * ) Notice: Subject to any disclaimer, the term of this patent is extended or adjusted under 35 U.S.C. 154(b) by 792 days.

(21) Appl. No.: 16/977,095

(22) PCT Filed: May 22, 2020

(86) PCT No.: PCT/CN2020/091843
§ 371 (c)(1),
(2) Date: Sep. 1, 2020

(87) PCT Pub. No.: WO2021/036366
PCT Pub. Date: Mar. 4, 2021

(65) Prior Publication Data
US 2023/0128148 A1    Apr. 27, 2023

(30) Foreign Application Priority Data

Aug. 29, 2019  (CN) .......................... 201910820650.3
Dec. 4, 2019   (CN) .......................... 201911229101.5
Dec. 31, 2019  (CN) .......................... 201911421531.7

(51) Int. Cl.
*A61N 5/10*      (2006.01)
*G16H 20/40*    (2018.01)

(52) U.S. Cl.
CPC ......... *A61N 5/1031* (2013.01); *A61N 5/1036* (2013.01); *A61N 5/1039* (2013.01);
(Continued)

(58) Field of Classification Search
CPC .. A61N 5/1031; A61N 5/1036; A61N 5/1039; A61N 5/1048; A61N 2005/1034; A61N 2005/1041; G16H 20/40
See application file for complete search history.

(56) References Cited

U.S. PATENT DOCUMENTS

2007/0003011 A1* 1/2007 Lane .................... A61N 5/1031
                                                          378/65
2018/0369611 A1* 12/2018 Owens ................ A61N 5/1031

FOREIGN PATENT DOCUMENTS

CN       105930636 A      9/2016
CN       107403201 A     11/2017
(Continued)

OTHER PUBLICATIONS

Decision on Rejection, issued in Chinese priority application No. 201910820650.3, dated Jun. 1, 2022.
(Continued)

*Primary Examiner* — Kiho Kim
(74) *Attorney, Agent, or Firm* — Zhu Lehnhoff LLP

(57) ABSTRACT

A standardized artificial intelligence automatic radiotherapy planning method includes acquiring a medical image; automatically delineating an ROI area of the medical image to acquire a geometric anatomical structure; determining a prescription according to disease type information corresponding to the medical image, the geometric anatomical structure, and a preset disease-prescription template library, and determining a radiation angle of radiation therapy; obtaining a radiation therapy dose distribution result using a dose prediction model; performing optimization processing
(Continued)

using a reverse optimization algorithm based on dose distribution or DVH guidance, with reference to the radiation dose distribution result, to generate executable radiation therapy plans.

20 Claims, 11 Drawing Sheets

(52) U.S. Cl.
CPC ........... *A61N 5/1048* (2013.01); *G16H 20/40* (2018.01); *A61N 2005/1034* (2013.01); *A61N 2005/1041* (2013.01)

(56) References Cited

FOREIGN PATENT DOCUMENTS

| CN | 108717866 A | | 10/2018 | |
| CN | 109771843 A | | 5/2019 | |
| CN | 109801696 A | | 5/2019 | |
| CN | 110415785 A | * | 11/2019 | ........... G06N 3/0454 |
| CN | 110415785 A | | 11/2019 | |
| CN | 111028914 A | | 4/2020 | |

OTHER PUBLICATIONS

Second Examination Report, issued in CN2019108206503 (priority application), by CNIPA, dated Feb. 22, 2022.
Examination Report, issued in CN2019108206503 (priority application), by CNIPA, dated Sep. 27, 2021.
Search Report, issued in CN2019108206503 (priority application), by CNIPA, dated Sep. 27, 2021.
International Search Report in PCT/CN2020/091843, issued by ISA, dated May 22, 2020.
Written Opinion of the International Search Report in PCT/CN2020/091843, issued by ISA, dated Aug. 25, 2020.

* cited by examiner

Table A.3 dose target of simulated head and neck tumor plan

| Planning parameters | Dose target cGy |
|---|---|
| Head and neck PTV D90 | >5 000 |
| Head and neck PTV D99 | >4 850 |
| Head and neck PTV D20 | <5 500 |
| Maximum dose Spinal cord | <4 000 |
| Parotid gland D50 | <3 000 |

```
▼ Chest4:
    ▶ PTV:       {...}
    ▶ LUNGL:     {...}
    ▼ LUNGR:
        0:       "LUNG-R"
        1:       "LUNG_R"
        2:       "Lung-R"
        3:       "Lung_R"
        4:       "Lung_R1"
    ▶ HEART:     {...}
    ▼ BREASTR:
        0:       "BREAST"
        1:       "BREAST-R"
        2:       "R-BREAST"
        3:       "breast c"
        4:       "breast-R"
        5:       "c-breads"
    ▶ CORD:      {...}
    ▶ HUMERUS:   {...}
    ▶ BODY:      {...}
▶ HN:            {...}
```

Figure 18 entering a dose editing mode when a dose editing trigger instruction is received

↓ a section graph of a spatial dose model on a current radiation therapy image section moves with a trajectory of a control cursor

↓ monitoring action events of the action control device, and adjusting a dose at a center of the spatial dose model according to a preset control command corresponding to the action events

↓ calculating doses at other points in the spatial dose model by interpolation on basis of the dose at the center of the spatial dose model

↓ saving and updating dose data at each point in the spatial dose model, without amendment to dose data in an area outside the spatial dose model

Figure 19

STANDARDIZED ARTIFICIAL INTELLIGENCE AUTOMATIC RADIATION THERAPY PLANNING METHOD AND SYSTEM

FIELD OF THE DISCLOSURE

The present disclosure relates to the field of smart medical technology, in particular, to a standardized artificial intelligence automatic radiation therapy planning method and a standardized artificial intelligence automatic radiation therapy planning system.

BACKGROUND OF THE DISCLOSURE

Tumor radiation therapy has become one of the main methods of breast cancer treatment, and has become one of the three major methods of tumor treatment. Its key purpose is to reduce the dose deposition at surrounding normal tissues as much as possible while ensuring that the prescribed dose is achieved in the target volume. Dosimetry verification is the main method of current clinical radiation therapy technology quality control and quality audit. Similarly, in the process of making radiation therapy plans, dose volume is also a main indicator to evaluate plan quality and forecast standards. However, the quality of radiation therapy plans is limited by the accumulation of experiences of plan designers, so that different institutions make considerably different delineation of target volumes of different breast types and different equipment used in the plan design, making it hard to guarantee consistency of plan quality. At the same time, clinical plans, mostly subject to group-based norms and standards, cannot provide patients with individualized treatment plans. Nowadays, three-dimensional dose distribution prediction models are divided into those based on BP (back propagation) neural networks and those based on deep convolutional networks. But the three-dimensional dose distribution prediction method based on BP neural networks requires manual extraction of features, which leads to a strong subjectivity in feature selection. Moreover, prescriptions and radiation angles of the above methods need to be determined by experienced doctors and physicists, and fully automatic dose prediction cannot be achieved.

There are several automated methods for treatment planning: KBP (Knowledge-based planning)-based method, PB-AIO (Protocol-based Automatic Iterative Optimization)-based method, MCO (Multi-Criteria Optimization)-based method and artificial intelligence-based automatic radiation therapy planning method.

However, the KBP-based method requires careful adjustment and optimization of the model, otherwise the tumor fitness and target coverage are not as good as the original manual plans; the predicted plans are only clinically acceptable, not certainly optimal; in the automatic optimization method based on PB-AIO, parameters of the input template directly determine the quality of the plans. If the template parameters are not set well enough, automatically generated plans will not be as good as those made by an experienced physicist through manual optimization. Accordingly, use of the method is limited by experiences of physicists. The MCO-based method is divided into a posterior method and a priori method. The priori method is still in the category of automation, in which no AI method is applied, and the radiation therapy plans resulted therefrom are mechanical, lacking plan evaluation and three-dimensional dose verification. It is impossible to ensure excellence and reliability of the plans. The plans obtained by the posterior method are the Pareto optimal solution within the flux range, which, however, fail to directly consider optimization of the machine parameters. The final plans need to be converted into those suitable for treatment, while dose characteristics will be changed in the process of the conversion. Particularly, remarkable dose differences will occur before and after the conversion in the cases where low-density tissues are present on the target volume. At this time, manual participation is required to adjust the parameters carefully.

In addition, the dose generation in the existing radiation therapy planning systems is achieved through dose optimization and dose calculation algorithms, which indirectly affect the dose distribution by adjusting algorithm control parameters, dose volume constraint parameters or biological constraint parameters, or editing flux or leaf sequence, etc. The dose optimization and dose calculation algorithm takes a long time, there are too many adjustable planning parameters, the planning adjustment strategy is not clear, and the way of the indirect adjustment parameters affecting the dose distribution is not intuitive, the planning design process requires repeated parameter adjustment and dose optimization, and the planning design efficiency is not high.

SUMMARY OF THE DISCLOSURE

For solution of at least one of the above problems, the present disclosure provides a standardized artificial intelligence automatic radiation therapy planning method and system, which, on the basis of the prediction model based on the geometric anatomy and the three-dimensional dose distribution of organs, introduces a prescription dose prediction model and automatic exposure angle optimization process, realizing fully automatic dose prediction and improving efficiency and effect of the dose prediction, so as to generate high-quality and fast executable radiation therapy plans with good accuracy, stability and standardization, thereby improving utilization of medical software and hardware resources.

In order to achieve the above objective, the present disclosure provides a standardized artificial intelligence automatic radiation therapy planning method, including: acquiring a medical image; automatically delineating an ROI (region of interest) area of the medical image to acquire a geometric anatomical structure; determining a prescription according to disease type information corresponding to the medical image, the geometric anatomical structure, and a preset disease-prescription template library; determining a radiation angle of radiation therapy according to the disease type information, the geometric anatomical structure and the prescription; inputting the medical image, the geometric anatomical structure, the disease type information, the prescription and the radiation angle of radiation therapy into a dose prediction model to obtain a radiation dose distribution result; performing optimization processing using a reverse optimization algorithm based on dose distribution or DVH guidance, with reference to the radiation dose distribution result, to generate executable radiation therapy plans; and the executable radiation therapy plans include forward radiation therapy plans, stereotactic radiation therapy plans and intensity-modulated radiation therapy plans, wherein the intensity-modulated radiation therapy plans include dynamic intensity-modulated radiation therapy plans, static intensity-modulated radiation therapy plans, volume-intensity-modulated radiation therapy plans, and rotational intensity-modulated radiation therapy plans.

In the above technical solution, preferably, the radiation therapy planning method further includes: scoring the generated executable radiation therapy plan through combination of unified prescription standards and artificial intelligence to obtain a total score of plan evaluation; performing 2D or 3D Gamma analysis on the generated executable radiation therapy plan using Monte Carlo three-dimensional dose verification technology, to obtain a pass rate of the Gamma analysis; automatically generating a radiation therapy plan report based on the executable radiation therapy plan, the total score of plan evaluation and the pass rate of the Gamma analysis; and a doctor reviews the radiation therapy plan report.

In the above technical solution, preferably, with respect to the radiation dose distribution result, the method further includes: entering a dose editing mode when a dose editing trigger instruction is received; a section graph of a spatial dose model on a current radiation therapy image section moves with a trajectory of a control cursor, wherein position of the control cursor is a center of the spatial dose model, and the trajectory of the control cursor corresponds to a moving trajectory of an action control device; monitoring action events of the action control device, and adjusting a dose at a center of the spatial dose model according to a preset control command corresponding to the action events; calculating doses at other points in the spatial dose model by interpolation on basis of the dose at the center of the spatial dose model; and saving and updating dose data at each point in the spatial dose model, without amendment to dose data in an area outside the spatial dose model.

In the above technical solution, preferably, said automatically delineating an ROI area of the medical image to acquire a geometric anatomical structure particularly includes: automatic identification and automatic delineation of normal organs: automatically identifying and delineating various normal organs of human body based on machine learning; automatic identification and delineation of tumor site: delineating tumors in reverse if the whole body organs are able to be delineated; after delineation of organs at risk is completed, remaining part will be the tumor site; and the remaining part is automatically delineated using relationship between PTV (Planning Target Volume) expansion and GTV (Gross Tumor Volume) expansion acquired by machine learning; said determining a radiation angle of radiation therapy according to the disease type information In the above technical solution, preferably, said determining a radiation angle of radiation therapy according to the disease type information, the geometric anatomical structure and the prescription specifically includes: performing machine learning on the disease type information, the geometric anatomical structure and the prescription of historical cases, determining a radiation angle prediction model, and inputting the disease type information, the geometric anatomical structure and the prescription of a current case into the radiation angle prediction model to obtain a predicted radiation angle as the radiation angle of radiation therapy; or marking an organ weight of a planned target volume according to disease type, calculating a cumulative value of organ weights at all angles in a ray direction, merging adjacent angles that meet a preset weight threshold, and using the angles that meet the weight threshold as the radiation angle of radiation therapy; or determining regions of interest, selecting at least one planned target volume and one organ at risk, and performing full-angle radiation projection for each region of interest; calculating a minimum bounding rectangle over the planned target volume at each angle of each segmented angle, and calculating an intersection between a minimum bounding rectangle of a certain organ at risk at the angle and the corresponding minimum bounding rectangle to obtain an intersection area; summing intersection areas of all segmented angles, taking the smallest sum as an objective function, and using a nonlinear integer optimization algorithm for solution to obtain an optimal segment index and an optimal angle index to serve as the radiation angle of radiation therapy.

In the above technical solution, preferably, a method for constructing the dose prediction model includes: establishing a data set with a normalized PTV average dose, and formulating a scoring template based on the data set; carrying out standardized naming for the region of interest; dividing a 3D medical image into 2D slices as a training set and a test set; reading out a beam angle of a 3D planned target volume data of the training set, and projecting the beam angle on the planned target volume to obtain a network weigh, and using a dose calculation algorithm to perform calculation on the network weight to obtain a beam channel; constructing a Pix2pix dose prediction model using a U-net network or a V-net network as a generator, and a Markov discriminator as a discriminator; using the 2D slice image as input of the generator, using predict dose and raw dose outputted by the generator as input of the discriminator, and outputting a discrimination result by the discriminator; and inputting all 2D slices of the training set into the Pix2pix dose prediction model for training.

In the above technical solution, preferably, said performing optimization processing using a reverse optimization algorithm based on dose distribution or DVH guidance, with reference to the radiation dose distribution result, to generate executable radiation therapy plans specifically includes: optimizing a flux weight map based on a flux map optimization algorithm; and then automatically generating an executable dynamic intensity modulated radiation therapy plan by a leaf sequence algorithm in combination with machine information of an accelerator; or, automatically generating an executable static intensity modulated radiation therapy plan based on a direct subfield optimization method; or, automatically generating a volume intensity modulated radiation therapy plan or a rotational intensity modulated radiation therapy plant based on genetic algorithm or column generation algorithm; or, a forward radiation therapy plan; or, a stereotactic radiation therapy plan.

In the above technical solution, preferably, said adjusting a dose at a center point of the spatial dose model according to a preset control command corresponding to the action events specifically includes: when the action events are monitored, a dose adjustment indication label is floating displayed; when it is monitored that the action control device is triggered with a first action event when the control cursor is located in an area of the dose adjustment indication label, a dose value corresponding to the position where the control cursor is located is taken as the dose at the center point of the spatial dose model; when it is monitored that the action control device is triggered with a second action event when the control cursor is located on an indication slide on the dose adjustment indication label, a dose value corresponding to position of the control cursor when clicking the second action event is released is used as the dose at the center point of the spatial dose model; when it is monitored that the action control device is triggered with a third action event when the control cursor is in the current section graph, action parameters of the third action event are used for adjusting the dose at the center point of the spatial dose model; and when it is monitored that the action control device is triggered with the third action event when the control cursor is not in the current section graph, a radiation therapy image is turned over with the action parameters of the third action event, and when it is removed from the area of the section graph, the dose adjusted by the third action event is saved.

In the above technical solution, preferably, the radiation therapy planning method further includes: monitoring the action event of the action control device, and according to the preset control command corresponding to the action event, the radiation therapy image where the spatial dose model is located can also be turned over, and the size of the spatial dose model can be adjusted; when it is monitored that a fourth action event is triggered by the action control device, the size of the spatial dose model is adjusted according to the action parameters of the fourth action event.

In the above technical solution, preferably, upper limit Dl and lower limit Du of the dose adjustment at the center point of the spatial dose model are respectively:

$$Dl = \begin{cases} D0 - n*R, & D0 - n*R \geq 0 \\ 0, & D0 - n*R < 0 \end{cases}$$

$$Du = \begin{cases} D0 + n*R, & D0 + n*R \leq Dmax \\ Dmax, & D0 + n*R > Dmax \end{cases}$$

wherein, Dl is a lower limit of the adjustable dose, Du is an upper limit of the adjustable dose, D0 is the dot dose at the center of the spatial dose model when the action event of the action control device is triggered, R is the characteristic parameter of the spatial dose model, and Dmax is the global maximum dose value of the dose data, n is a constant.

The present disclosure also provides a standardized artificial intelligence automatic radiation therapy planning system, for implementing the standardized artificial intelligence automatic radiation therapy planning method according to any one of the above technical solutions.

Compared with the prior art, the present disclosure has the following beneficial effects: on the basis of the prediction model based on the geometric anatomical structure and the three-dimensional dose distribution of organs, introducing automatic optimization process of the prescription dose prediction model and the radiation angle to realize the fully automatic dose prediction, which improves the efficiency and effect of dose prediction, so that an executable radiation therapy plan can be generated quickly and with high quality, with good accuracy, stability and standardization, thereby improving the utilization of medical software and hardware resources. In addition, the method of directly editing the dose allows users to visually and directly obtain the desired dose distribution, which is faster and more visual than the method of indirectly adjusting parameters to influence the dose distribution and greatly improves efficiency of the planning design.

BRIEF DESCRIPTION OF THE DRAWINGS

FIG. 18 is a list of mapping dictionaries of standard names and aliases disclosed in an embodiment of the present disclosure;

FIG. 19 is a flowchart of a dose editing method disclosed in an embodiment of the present disclosure;

DETAILED DESCRIPTION OF THE EMBODIMENT(S) OF THE DISCLOSURE

In order to make the objectives, technical solutions, and advantages of the embodiments of the present disclosure clearer, the technical solutions in the embodiments of the present disclosure will be described clearly and completely with reference to the drawings of the embodiments of the present disclosure. Obviously, the described embodiments only are part of the entire embodiments of the present disclosure. Based on the embodiments of the present disclosure, all other embodiments obtained by those of ordinarily skilled in the art without creative work shall fall into the protection scope of the present disclosure.

Figure 1:
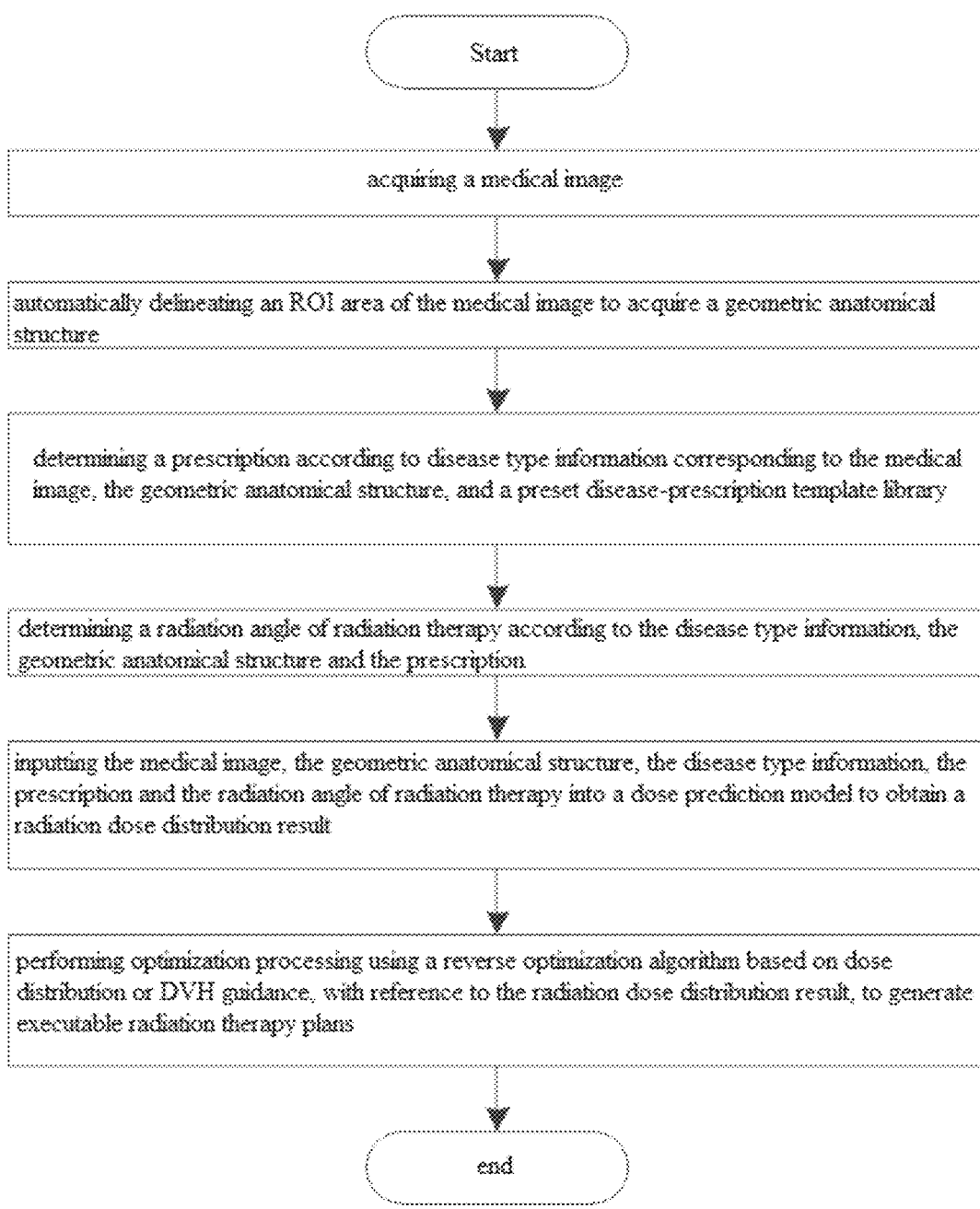
FIG. 1 is a schematic flowchart of a standardized artificial intelligence automatic radiation therapy planning method disclosed in an embodiment of the present disclosure.

The present disclosure will be further described in detail below with reference to the drawings:

As shown in FIG. 1, a standardized artificial intelligence automatic radiation therapy planning method according to the present disclosure includes: acquiring a medical image; automatically delineating an ROI area of the medical image (such as CT, MR images) to acquire a geometric anatomical structure; determining a prescription according to disease type information corresponding to the medical image, the geometric anatomical structure, and a preset disease-prescription template library; determining a radiation angle of radiation therapy according to the disease type information, the geometric anatomical structure and the prescription; inputting the medical image, the geometric anatomical structure, the disease type information, the prescription and the radiation angle of radiation therapy into a dose prediction model to obtain a radiation dose distribution result; performing optimization processing using a reverse optimization algorithm based on dose distribution or DVH guidance, with reference to the radiation dose distribution result, to generate executable radiation therapy plans; the executable radiation therapy plans include forward radiation therapy plans, stereotactic radiation therapy plans and intensity-modulated radiation therapy plans, wherein the intensity-modulated radiation therapy plans include dynamic intensity-modulated radiation therapy plans, static intensity-modulated radiation therapy plans, volume-intensity-modulated radiation therapy plans, and rotational intensity-modulated radiation therapy plans.

In this embodiment, specifically, on the basis of the prediction model based on the geometric anatomical structure and the three-dimensional dose distribution of organs, a prescription dose template and an automatic angle optimization process are added to realize fully automatic dose prediction; the specific process is as follows:

(1) Medical image acquisition: obtaining a patient image through CT machine or nuclear magnetic (MR) and storing the same in a preset format; preferably, establishing an OIS (oncology information system) to manage the patient images, patient information and treatment information, preferably using a Dicom standard;

(2) Organ delineation: automatically delineating the acquired medical image to obtain a geometric anatomical structure, where the delineation process includes delineation of normal organs and tissues and delineation of tumor target volumes;

(3) Prescription determination: automatically determining a prescription according to the above delineation information and disease type information; the prescription is determined by mapping relationship between the prescription and diseases in the preset disease-prescription template library, which disease-prescription template library shall be defined in advance;

(4) Angle determination: automatically determining a radiation angle using the prescription, the disease type, and the delineation information;

(5) Dose prediction: completing model training before dose prediction, wherein the model training only requires one training, and in daily use the dose prediction can be completed just by inputting data in a set format, wherein, preferably, the dose prediction model is a dose prediction model based on Pix2pix-based patient's geometric anatomical structure and three-dimensional dose distribution of organs, and the input data adopts the Dicom standard format;

(6) Output results and display: the generated prediction results can be verified through such aspects as average change rate of the target volume, DVH comparison, predict dose image comparison, and Dice similarity coefficient, and the dose prediction results provide more sufficient data information to subsequent plan optimization and plan quality control.

On this basis, through combination of AI and radiation therapy planning data sets, a deep learning neural network model is established, and a high quality automatic planning model can be generated after training with excellent radiation therapy planning data sets through deep learning methods, with which model radiation therapy plan prediction can be performed according to medical images input by users. The above-mentioned whole process is completed without human intervention, and only machine time of computers is occupied, thereby greatly improving efficiency of producing radiation therapy plans, considerably reducing patient's waiting time for treatment, and indirectly improving the curative effect.

In the above embodiment, preferably, said automatically delineating an ROI area of the medical image (such as CT, MR images) to acquire a geometric anatomical structure particularly includes: automatic identification and automatic delineation of normal organs: automatically identifying and delineating various normal organs of the human body based on machine learning; automatic identification and delineation of tumor site: delineating the tumor in reverse if the whole body organs are able to be delineated; after delineation of organs at risk is completed, the remaining part will be the tumor site; and the remaining part is automatically delineated using relationship between PTV expansion and GTV expansion acquired by machine learning.

In this embodiment, specifically, the automatic target volume delineation based on deep learning can realize:

1. Automatic identification and automatic delineation of normal organs (organs at risk): various organs of the human body can be automatically delineated based on machine learning;

2. Automatic identification and delineation of the tumor site: if organs of the whole body are able to be delineated, the tumor will be delineated in reverse; after the delineation of the organs at risk is completed, the remaining part will be the tumor site, and the remaining part is automatically delineated using relationship between PTV expansion and GTV expansion acquired by machine learning.

Specifically, firstly an ROI of interest is determined from the ROI under delineation, and at least one PTV and one OAR (Organ At Risk) are selected. For each ROI, projection is performed within a beam angle range of 0-360 degrees, a set of initial segments (representing the position of JAW; denoted by i for index) are given, and to each segment is given a set of initial angles (denoted by j for index). At an angle within a segment, a minimum bounding rectangle is obtained with respect to PTV(i, j) (treatment plan target volume), recorded as block (i, j). For a certain OAR (denoted by k for index), intersection of block (i, j) is calculated with this angle and this segment, thereby obtaining an intersection area. A sum of all intersection areas of OAR and block (i, j) of this segment is calculated, and then sums of all segments are obtained, recorded as Sall. Taking the minimum Sall result as an objective function, a non-linear integer optimization algorithm is used to obtain an optimal segment index and an optimal angle index. The above steps finally optimize a best lead gate position and a best radiation angle. On the basis of sufficient exposure at PTV, the exposure to OAR caused by radiation leak is fully reduced. This algorithm is proposed based on the point of conforming with basic principles of making radiation therapy plans, which fully protects normal tissues.

In the above-mentioned embodiment, preferably, there are three methods for determining a radiation angle of radiation therapy according to the disease type information, the geometric anatomical structure and the prescription, which three methods specifically include:

(1) Performing machine learning on the disease type information, the geometric anatomical structure and the prescription of historical cases, determining the radiation angle prediction model, and inputting the disease type information, the geometric anatomical structure and the prescription of a current case into the radiation angle prediction model to obtain a predicted radiation angle as the radiation angle of radiation therapy;

(2) Marking an organ weight of the planned target volume according to the disease type, calculating a cumulative value of the organ weights at all angles in a ray direction, merging adjacent angles that meet a preset weight threshold, and using the angles that meet the weight threshold as the radiation angle of radiation therapy;

Specifically, the organ weights of different disease types are marked according to different disease types. The larger the weight is, the more important it is. The tumor target volume is marked as 0. The organ weight can be divided into given organ sub-weights. Weight marking can be determined using a reciprocal of a maximum allowable exposure dose of an organ. The larger the maximum allowable exposure dose, the smaller the weight. In the process of determining weight of the angle, the organ weight or sub-weight accumulated value of each angle is calculated according to the preset angle interval in the ray direction. When selecting an angle that meets the weight threshold, if the number of angles is less than a preset minimum value, the default is the preset value, and if the angle is greater than a preset maximum value, the default is the maximum value.

(3) Determining regions of interest, selecting at least one planned target volume and one organ at risk, and performing full-angle radiation projection for each region of interest; calculating a minimum bounding rectangle over the planned target volume at each angle of each segmented angle, and calculating an intersection between a minimum bounding rectangle of a certain organ at risk at the angle and the corresponding minimum bounding rectangle to obtain an intersection area; summing intersection areas of all segmented angles, taking the smallest sum as an objective function, and using a nonlinear integer optimization algorithm for solution to obtain an optimal segment index and an optimal angle index to serve as the radiation angle of radiation therapy.

In the above embodiment, the Beam angle is also called beam angle or beam direction. The purpose of radiation therapy is to deliver a dose high enough to the planned target volume to control the tumor, while ensuring that the surrounding normal tissues and organs at risk (OARs) are at an acceptable dose level to avoid damage. In precision treatment, setting of the beam angle impacts the exposure dose of the planned target volume and the organ at risk, which has an important influence on quality of the treatment plan. Due to the influence of curved surface and uneven tissue of human body on dose distribution, it is difficult to determine an angle of radiation field during design of treatment plans, so that determining the most suitable radiation field incidence direction for each patient becomes a time-consuming and trial-and-error process. Therefore, considering the beam angle during the training process helps to predict a dose distribution map more accurate and more suitable for meeting clinical requirements.

Figure 2:
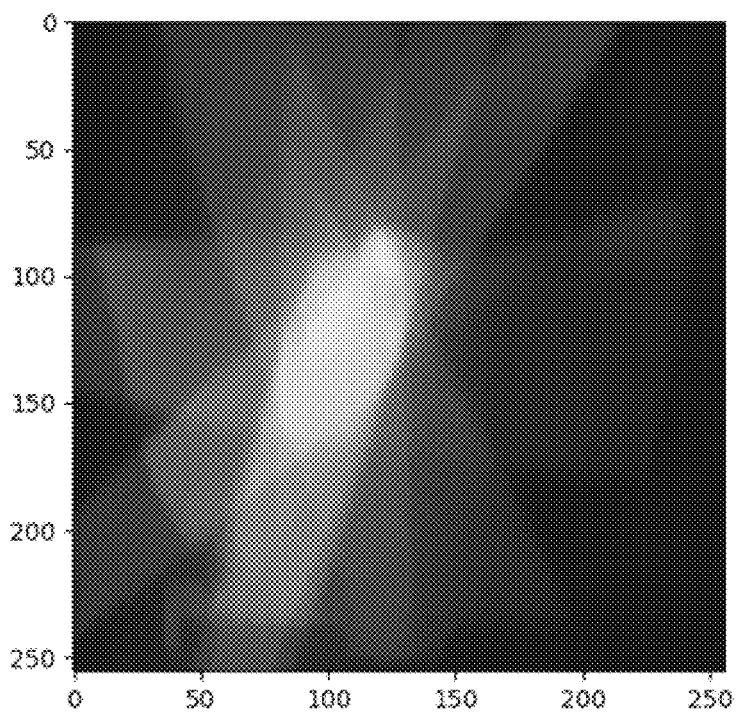
FIG. 2 is a schematic diagram of the image display of the Beam channel disclosed in an embodiment of the present disclosure.

The method of generating the Beam channel is as follows: first taking out 3D PTV data, reading out the Beam angle contained in the case, and projecting the angle of radiation field on the PTV to obtain a network weight of beam channel data (here the area falling into the range of radiation field will be set as 1, and the others as 0), and using a high-speed dose calculation algorithm to directly perform dose calculation on the network weight to obtain a Beam channel. Image display of the generated Beam channel is shown in FIG. 2.

In the above embodiment, preferably, a dose prediction model based on Pix2pix is used. The method for constructing a dose prediction model includes: establishing a data set with a normalized PTV average dose, and formulating a scoring template based on the data set; carrying out standardized naming for the region of interest; dividing a 3D medical image into 2D slices as a training set and a test set; reading out a beam angle of a 3D planned target volume data of the training set, and projecting the beam angle on the planned target volume to obtain a network weigh, and using a dose calculation algorithm to perform calculation on the network weight to obtain a beam channel; constructing a Pix2pix dose prediction model using a U-net network or a V-net network as a generator, and a Markov discriminator as a discriminator; using a 2D slice image as input of the generator, using predict dose and raw dose outputted by the generator as input of the discriminator, and outputting a discrimination result by the discriminator; and inputting all 2D slices of the training set into the Pix2pix dose prediction model for training.

In this embodiment, specifically, the model training involves formulation of a scoring template, standardized naming of a region of interest, and a model training process. Pix2pix is a GAN-based image translation model. A GAN network contains a generator G and a discriminator D, which restrict and promote each other. The image generated by G and ground truth are handed over to D at the same time for discrimination, resulting in a probability that the generated image is an original image. If the probability is large, it shows that the image generated by G is very close to the original image, thus deceiving D; if it is discriminated as fake, it means that D has recognized that the generated image is quite different from the original image. In the above-mentioned gaming process between G and D, both have learned experiences, in which the fake image generated by G becomes more and more real, and the discrimination result of D becomes more and more correct. When D can no longer distinguish whether the image generated by G is real or fake, a set of well-trained dose prediction model is obtained. Preferably, iterative training of the dose prediction model is not completed until the convergence curve reaches a preset convergence value.

Specifically, this embodiment is the first to use the Pix2pix model and the Beam channel to predict radiation dose. Pix2pix is a GAN-based image translation model. A GAN network contains a generator G and a discriminator D, which restrict and promote each other. The image generated by G and ground truth are handed over to D at the same time for discrimination, resulting in a probability that the generated image is an original image. If the probability is large, it shows that the image generated by G is very close to the original image, thus deceiving D; if it is discriminated as fake, it means that D has recognized that the generated image is quite different from the original image. In the above-mentioned gaming process between G and D, both have learned experiences, in which the fake image generated by G becomes more and more real, and the discrimination result of D becomes more and more correct. When D can no longer distinguish whether the image generated by G is real or fake, a set of well-trained generation model is obtained.

Figure 3:
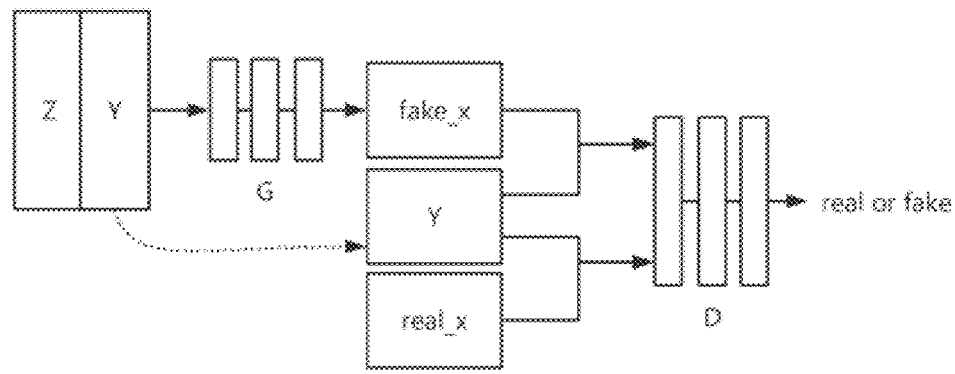
FIG. 3 is a schematic diagram of the principle of a cGAN generation network disclosed in an embodiment of the present disclosure.

As shown in FIG. 3, the input of cGAN generation network G includes noise Z and condition Y, and the output generates a fake_x. The input of the discrimination network D includes fake_x or real_x and condition Y, and the output is the discrimination result 0 or 1, namely, FAKE or REAL.

Figure 4:
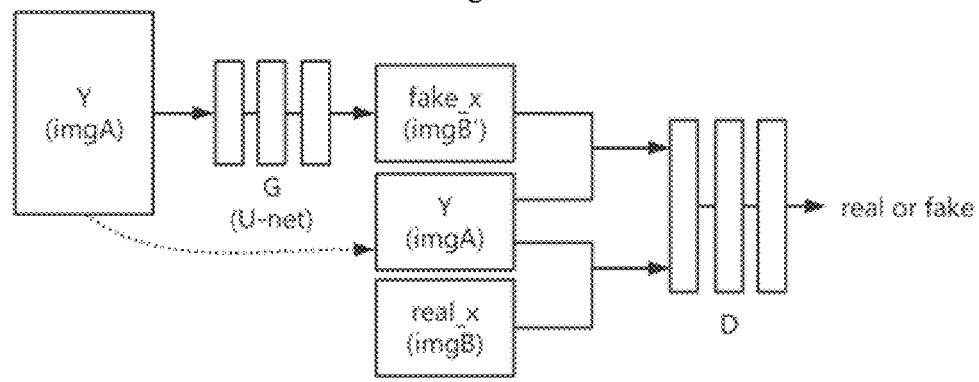
FIG. 4 is a schematic diagram of the principle of a Pix2pix generation network disclosed in an embodiment of the present disclosure.

As shown in FIG. 4, Pix2pix draws on the idea of cGAN. Not only noise but also a condition will be input into the G network, and the fake images generated by the G network will be affected by the specific condition. Taking an image as a condition, the generated fake images have a corresponding relationship with the condition images, thus realizing an image-to-image translation process. Specifically, the input terminal of the generation network G of Pix2pix has only one condition Y, where Y is an image imgA. The generation network G uses the U-net structure, and the input Y code is decoded into a real image imgB'. The input of the discriminator is the generated image imgB' or the real image real_x(imgB) and the condition Y, and finally the image-to-image translation is realized.

In this embodiment, the input Y is a 4-channel image, which, including a 3-channel dose image and a beam channel, obtains a predict dose fake_x through the U-net generator. The raw dose and the generated predict dose are put into the discriminator together to discriminate differences between the predict dose and the real dose and enter the discrimination result.

The structure of the generator and the discriminator used in this embodiment will be described in detail below.

Figure 5:
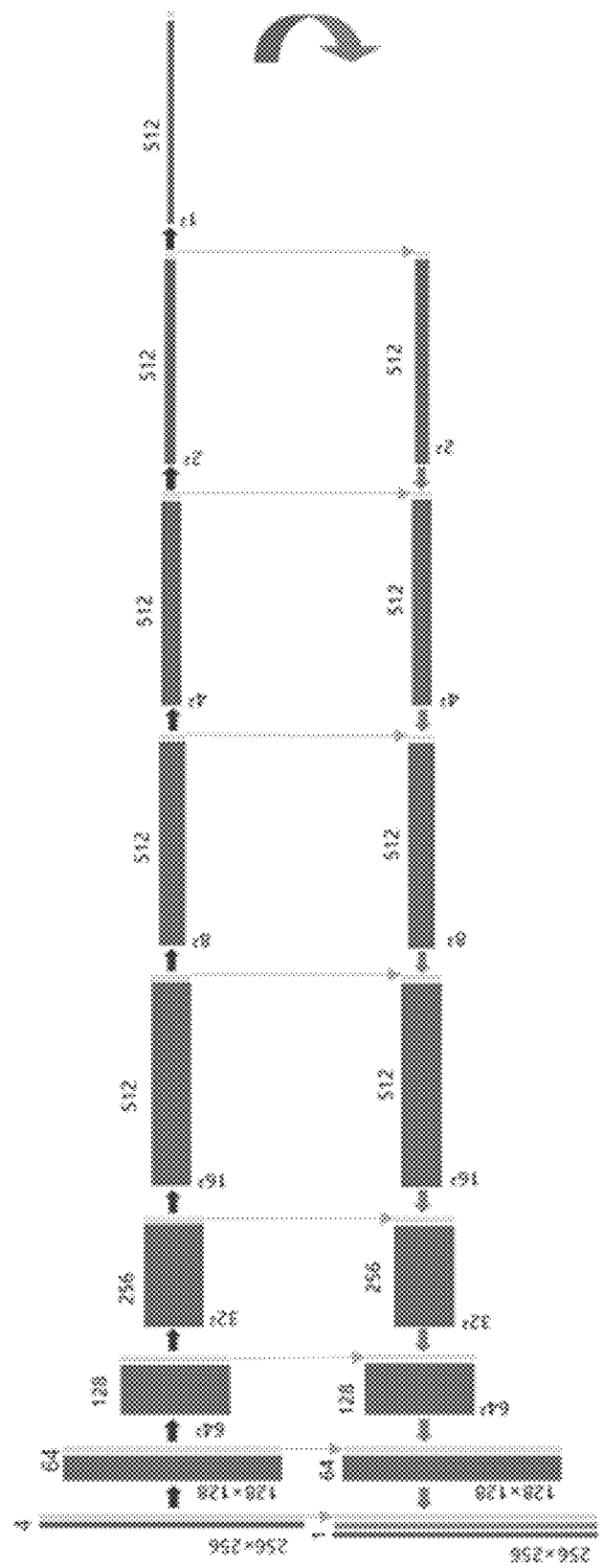
FIG. 5 is a schematic diagram of the principle of the generator model disclosed in an embodiment of the present disclosure.

As shown in FIG. 5, the generator in this embodiment uses an 8-level U-net to achieve the mapping from image to dose. The entire network structure can be regarded as a feature extraction part and an up-sampling part. The input starts with 4 channels of a 256×256 pixel image. The feature extraction part performs a 3×3 convolution operation for each layer, and uses a 2×2 maximum pooling layer to the next layer, so as to reduce the feature size of 256×256 pixels to 1×1 pixels. In the up-sampling part, the same convolution kernel is used to convolve each layer of data, and when entering the next layer, the maximum pooling layer becomes 2×2 deconvolution, so as to transform the size of the image into that of the original image. In order to keep the underlying information from being lost and the image detail information, the method shown in FIG. 5 is used to preserve the underlying features. The final output image is a dose map of 256×256×1.

In the training phase, Adam algorithm is selected as the optimizer to minimize the loss function. In this embodiment, the training is set into two stages, Adam parameters $\Delta 1=0.55$, $\Delta 2=0.999$. In the first stage, the learning rate is $2\times 10^{-5}$ and the epochs are 100; in the second stage, the learning rate is 2e-06 and the epochs are 300. This embodiment is divided into two stages of training. On the one hand, the convergence speed can be improved, and on the other hand, the training can be continued without affecting the result in the case of any interruption.

Figure 6:
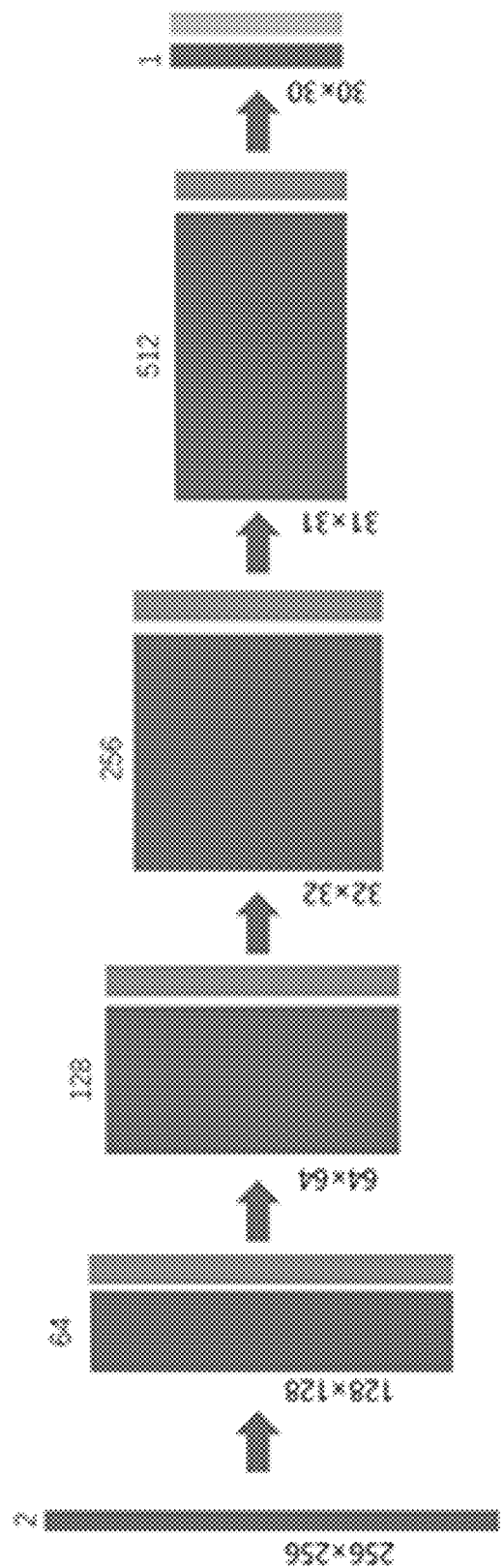
FIG. 6 is a schematic diagram of the principle of the discriminating process of the discriminator disclosed in an embodiment of the present disclosure.

The Markov discriminator (PatchGAN) shown in FIG. 6 could be used as the discriminator to determine whether it is a generated picture. Because different patches can be considered to be independent of each other, the idea of Patch-GAN is to let the discriminator judge the real and fake of each patch of N×N size in the image. Pix2pix cuts a picture into different patches of N×N size, and the discriminator judges whether each patch is real or fake, and averages the results of all patches of one picture as the final discriminator output. For 256×256 input, the judgment result is the best when the patch is of a 70×70 size.

Figure 7:
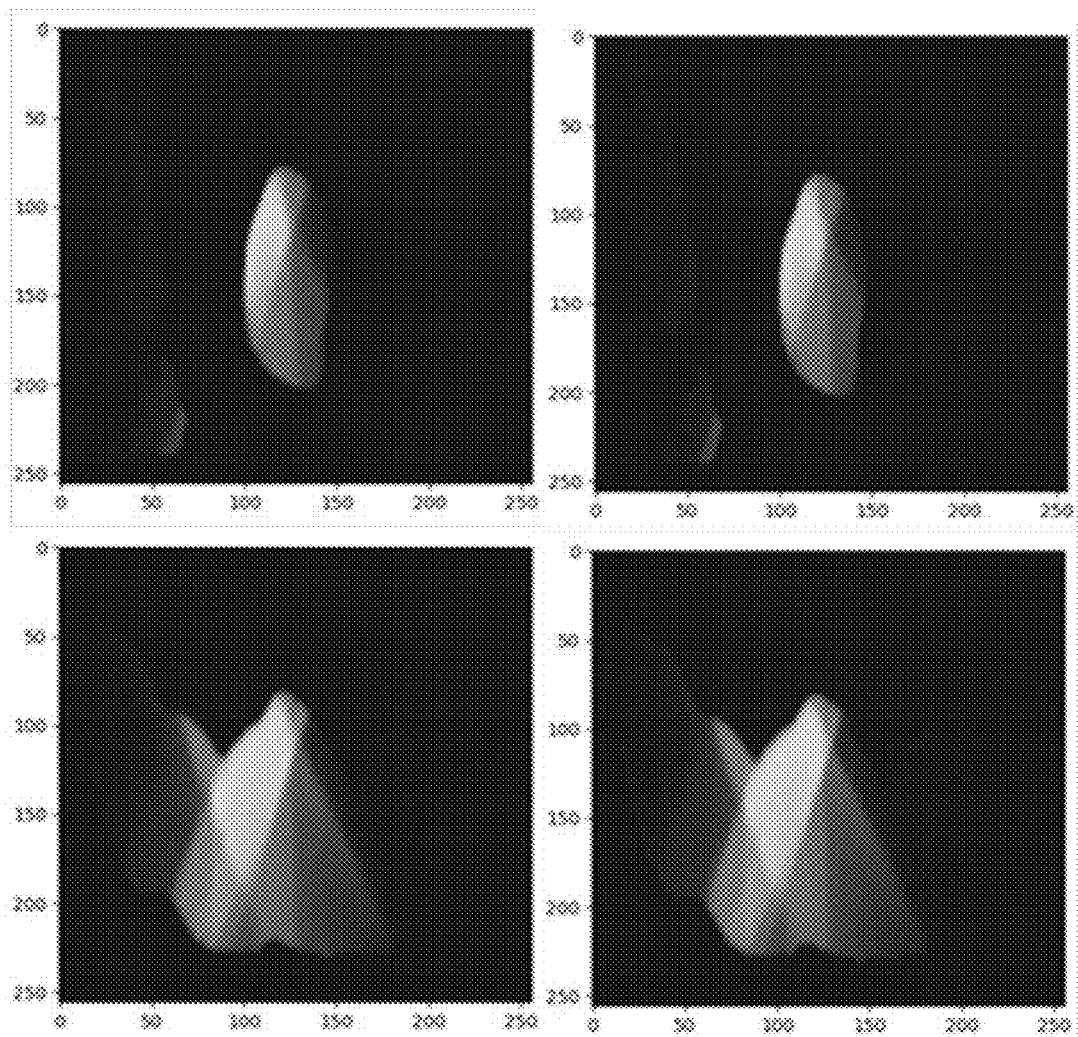
FIG. 7 is a schematic diagram of the comparison between the predict dose and the raw dose disclosed in an embodiment of the present disclosure.

As shown in FIG. 7, as a typical prediction example of the Pix2pix model, FIG. 7 shows the comparison between the predict dose image and the real dose image of the same case. On the left side is the predict dose image, and on the right is the raw dose image. It follows that, thanks to the fact that the generator uses the U-net network to save the underlying information, the detailed information of the predict dose image is preserved better.

Figure 8:
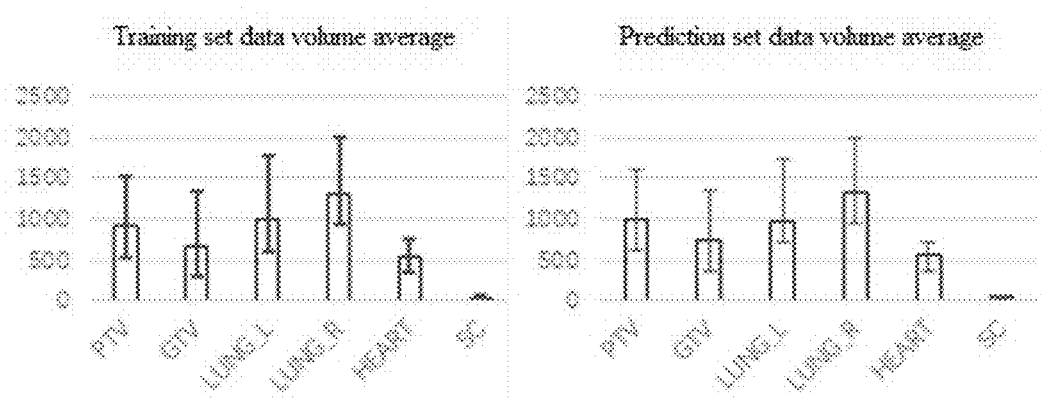
FIG. 8 is a schematic diagram of the comparison of data volume averages of the training set and the prediction set disclosed in an embodiment of the present disclosure.

In the present disclosure, taking the dose prediction process of breast cancer target volume radiation therapy as an example, in the dosimetry assessment, the difference between the receptor volumes will also affect the receptor dose. It can be seen from FIG. 8 that volume MEAN value of the planned target volume (PTV) of the training set is 915.46 cm$^3$, volume MEAN value of the GTV is 658.74 cm$^3$, volume MEAN value the left lung is 1001.09 cm$^3$, volume MEAN value of the right lung is 1315.38 cm$^3$, volume MEAN value of the heart is 533.33 cm$^3$, and volume MEAN value of the spinal cord is 40.95 cm$^3$. Volume MEAN value of the planned target volume (PTV) of the prediction set is 978.1 cm$^3$, volume MEAN value of the GTV is 743.06 cm$^3$, volume MEAN value of the left lung is 981.9 cm$^3$, volume MEAN value of the right lung is 1329 cm$^3$, volume MEAN value of the heart is 552.3 cm$^3$, and volume MEAN value of the spinal cord is 43 cm$^3$.

Figure 9:
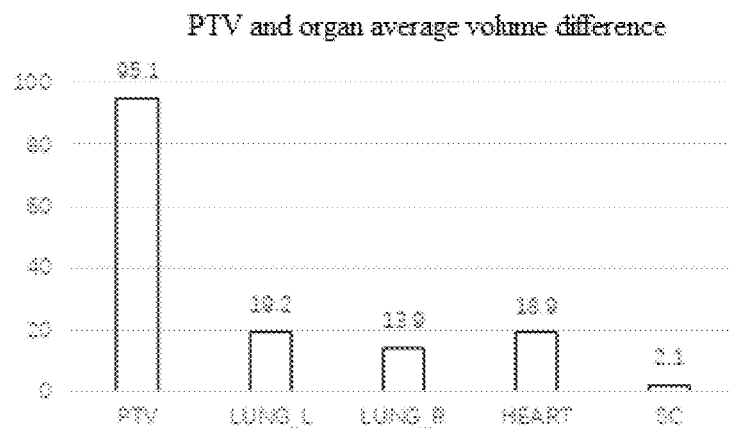
FIG. 9 is a schematic diagram of the comparison of the difference between the average organ volume of the training data and the prediction data disclosed in an embodiment of the present disclosure.

As shown in FIG. 9, in the above embodiment, the volume average value of each marked organ in the data is taken for comparison, and the calculation formula is $\text{predict}_{mean}-\text{raw}_{mean}$. The PTV volume difference reaches 95.1 cm$^3$, and the volume differences of the lungs, the heart, and the spinal cord all are less than 20 cm$^3$. Combining the volume differences with the dose change rate in Table 1, for the PTV area with a large volume difference, the dose change rate D2 and D98 are 0.33% and 3.55%, respectively. The predict dose is lower than the raw dose, but the dose average values of D95 all meet the prescription dose requirements and meet the clinical dose requirements. The left lung volume difference is small, and although the dose change rate reaches 8.19%, the base is only about 1.5 Gy, which is within the clinically acceptable range. The right lung belongs to a large receiving area, and based on a small volume difference, the dose change rate of V5, V10, and V20 are all less than 1%. Although the dose change rate of V30 reaches 12.5%, the difference between the predict dose average and the raw dose average is only 3.1 Gy, which falls into the clinically acceptable range. The dose difference of the spinal cord is about 2.8 Gy, and the volume difference is 2.1 cm$^3$, which is also within the clinically acceptable range.

As can be seen from analysis on the data in Table 1, the predict dose is generally smaller than the planned raw dose, but both of them meet the requirements of D95 satisfying the prescribed dose. Therefore, it is believed that the dose of some training data still has room to drop. The model fully considers the volume and dose of the organ at risk, learns and proposes a better dose distribution result.

TABLE 1

Comparison of rate of change between the predicted dose average and the raw dose average $$\text{RATE OF CHANGE} = \left| \frac{\text{RAW} - \text{PREDICT}}{\text{RAW}} \right| \times 100$$

| | PREDICT | RAW | RATE OF CHANGE |
|---|---|---|---|
| D2 | 54.52 | 54.71 | 0.33% |
| D95 | 49.92 | 50.21 | 0.57% |
| D98 | 46.24 | 46.91 | 1.42% |
| HI | 0.156 | 0.137 | 13.8% |
| CI | 1.619 | 1.469 | 10.2% |
| HEART_MEAN | 1.116 | 1.292 | 13.63% |
| LUNGL_MEAN | 1.58 | 1.721 | 8.19% |
| LUNGR_MEAN | 17.03 | 17.2 | 0.95% |
| LUNGR_V5 | 55.84 | 55.81 | 0.048% |
| LUNGR_V10 | 41.23 | 41.36 | 0.31% |
| LUNGR_V20 | 29.93 | 30.21 | 0.92% |
| LUNGR_V30 | 22.3 | 25.49 | 12.5% |
| SC_MAX | 27.03 | 28.86 | 6.33% |

Table 1 shows the comparison of rate of change between the predicted dose average and the raw dose average, wherein the calculation formula of HI and CI is:

$$HI = \frac{D_2 - D_{98}}{D_{MEAN}}, \quad CI = \frac{V_{95}}{V_{GTV}} \times \frac{V_{95}}{V_{PTV}}.$$

For these two indicators, the smaller the value of HI and the closer to 1 the value of CI is, the better the radiation therapy plan is made. For large-volume organs such as the left lung and right lung, the predicted rate of change is 0.12 in maximum. For small-volume organs such as the heart, although the rate of change is large, the actual difference between the predict dose average and the raw dose average data is only 0.176 Gy. The difference between the prediction data set and the raw data in the prediction result is within the clinically acceptable range, which is not large compared with the rate of change in the training set data.

Figure 10:
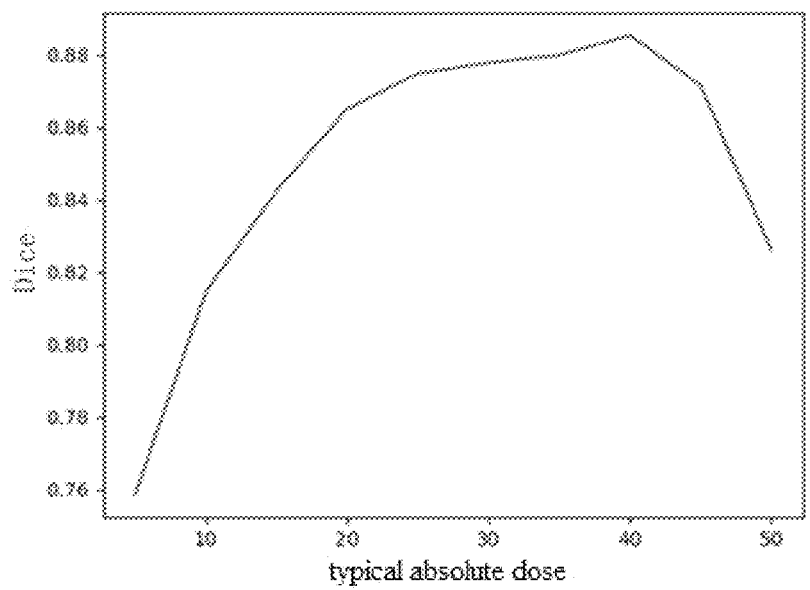
FIG. 10 is a schematic diagram of a dice similarity coefficient curve of the typical absolute dose disclosed in an embodiment of the present disclosure.

The similarity coefficient between the predict dose and the raw dose is expressed by the Dice similarity coefficient. It can be seen from FIG. 10 that in the absolute dose range of 3-50 Gy, the Dice value under the 20 Gy dose gradually rises between 0.76 and 0.86, and the Dice value in the 20-45 Gy range fluctuates between 0.86 and 0.9, and when the absolute dose is above 45 Gy the Dice value has a slow downward trend, which, however, remains above 0.83. Through data analysis, it is found that in right breast cancer, the low-dose area is mainly located in the spinal cord, the left lung and the heart, with a dose below 30 Gy, and the high-dose area is mainly located in the right lung and PTV. This complex target volume has the characteristics of uneven dose distribution and large dose span. Therefore, in the case of below an absolute dose below 20 Gy, the similarity coefficient is low, but the rate of change and the performance on DVH meet the clinical dose requirements in the low-dose region despite of the low similarity coefficient.

Dose-volume histogram (DVH) is a widely accepted treatment plan evaluation method in the current three-dimensional conformal radiation therapy, which visually represents the relationship between dose and volume in target volume and normal tissues. The DVH of the target volume can show the uniformity of irradiation, and the DVH of the normal tissues can provide the irradiated dose of the organ and its corresponding volume, which, in particular, have important clinical meanings for normal organs whose radiation tolerance is related to the irradiated volume. Dose volume index, as a method to evaluate the radiation therapy plan, has the characteristics of visually feeling dose changes. In the process of making radiation therapy plans, physicists can use the eclipse software to manually adjust the weight and dose on the DVH to monitor the dose change in real time. Through the image, it can be visually seen that the PTV curve and the BODY curve basically overlap, which ensures that the target volume is adequately exposed to the dose and the body dose is maintained within the clinically acceptable range.

Figure 11:
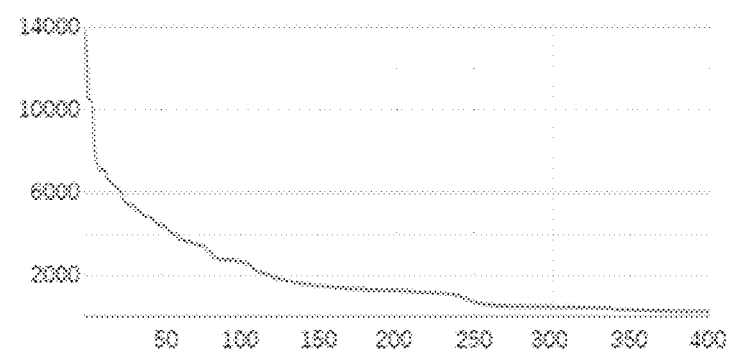
FIG. 11 is a schematic diagram of a loss curve of the iterative training disclosed in an embodiment of the present disclosure.

In general, in this example, 120 training samples and a total of approximately 12,000 training images are trained with a total epochs of 400 times. This process is run for 4×24 h on the gtx1080 graphics card. FIG. 11 shows a loss graph of the generation model. The loss of the training model is 13,800 at the beginning and dropped to 4210 after 50 iterations. After 300 iterations of training, the curve converges smoothly, and the loss of 350 iterations is reduced by 40 compared with 300 iterations. Finally, the model converges to 5 after 400 iterations. There is no greater fluctuation in the loss curve after the training is continued. This is the reason for choosing 400 iterations.

In summary, in the above embodiments, the dose prediction of complex target volume of breast cancer is realized by using Pix2pix in combination with the field angle. In this embodiment, the dose prediction is defined as an image coloring problem, and the Pix2pix dose prediction model performs well on this problem. Secondly, the Pix2pix dose prediction model is convenient to use in experiments for data pairing requirements. Finally, the generator in the model uses the U-net network, which retains the underlying information, providing a guarantee for the model to predict the details of the image. The experimental results show that by comparing the rate of change of the dose volume parameter of the target volume with the rate of change of the normal organ dose volume parameter, a clinically acceptable predict radiation therapy dose result is obtained.

In addition, in the process of constructing an automatic dose prediction model that considers the beam angle, if the difference in dose distribution caused by different beam angles can be considered, the training and prediction accuracy can be improved, and the problem of insufficient source of cases can also be solved; the algorithm is also critical for solving universality problem of the automatic dose prediction. A possible solution is to consider beam angles for both prediction and training. Specifically, there are several options as follows:

Solution I:

During training and predicting, beam angles are used as a prior condition, cases are marked, and a machine learning model with conditional probability is used for training and prediction. When making predictions, a user inputs a customized beam angle combination (because one plan has multiple beams, there are multiple beam angles, which is called a beam angle combination here). If the user does not input beam angles, the system can automatically give a set of recommended beam angles by default. The recommended value is a set of best beam angles found by a clustering method in the machine learning based on the cases involving the same disease type. It is also possible to establish a prediction model based on the anatomical characteristics of historical cases and images, and automatically predict an appropriate beam angle combination based on the input CT images. The model that can be referred to includes a conditional generation adversarial network CGAN, and an original generation adversarial network model has been implemented. Schematic diagram of the CGAN is shown in FIG. 3.

Figure 12:
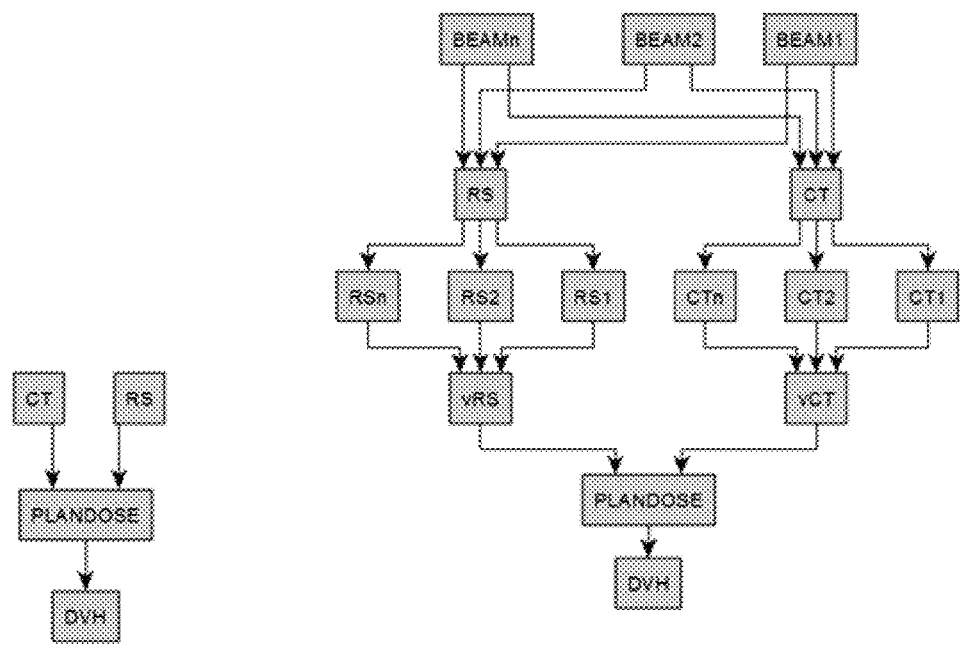
FIG. 12 is a flow chart of data preprocessing disclosed in an embodiment of the present disclosure.

Solution II:

Data preprocessing is performed on the input CT (and RS) before training and prediction. The parentheses here represent two possible solutions, i.e., the processing with RS and the processing without RS. Taking the processing with RS as an example, CT data is rotated, cut, sited and synthesized around a certain axis (gantry rotation axis is recommended) according to the beam angle (and the MU weight in the existing case plan, also taking the circumstance where MU weight is included as an example). The synthetization is based on MU as the weight, and the synthesized CT data is obtained by the center-of-gravity method. If the MU is not considered, the weight is set to 1. Finally, a virtual CT is reconstructed. For RS, the coordinates are rotated, and the final coordinates are generated with the rotated coordinates also by the center-of-gravity method, and the weights refer to the synthesis method of CT. The flowchart is shown in FIG. 12. The left figure represents the data preprocessing process without considering the beam angle; and the right figure uses the CT each having three slices as an example to illustrate the reconstruction process.

Solution III:

For case plans with different beam angles, the plans deviating from main beam combinations are screened out and discarded in a pre-processing method, wherein the screening is conducted with respect to the plans of historical cases as collected according to the formula proposed below.

$$\frac{\sum (MU \times |gA - 180|)}{\sum MU}$$

The screening is carried out with the standard of one time the standard deviation, and the excess cases are not used for training. The rest can be used as a training set. This method reduces the impact of different beam angles on the predict dose distribution to a certain extent, but it also reduces the cases that can be used for training to a certain extent. An example of 20 sets of planning cases is shown in the table below. First, all beam angles are extracted from the 20 sets of cases.

Figure 13:
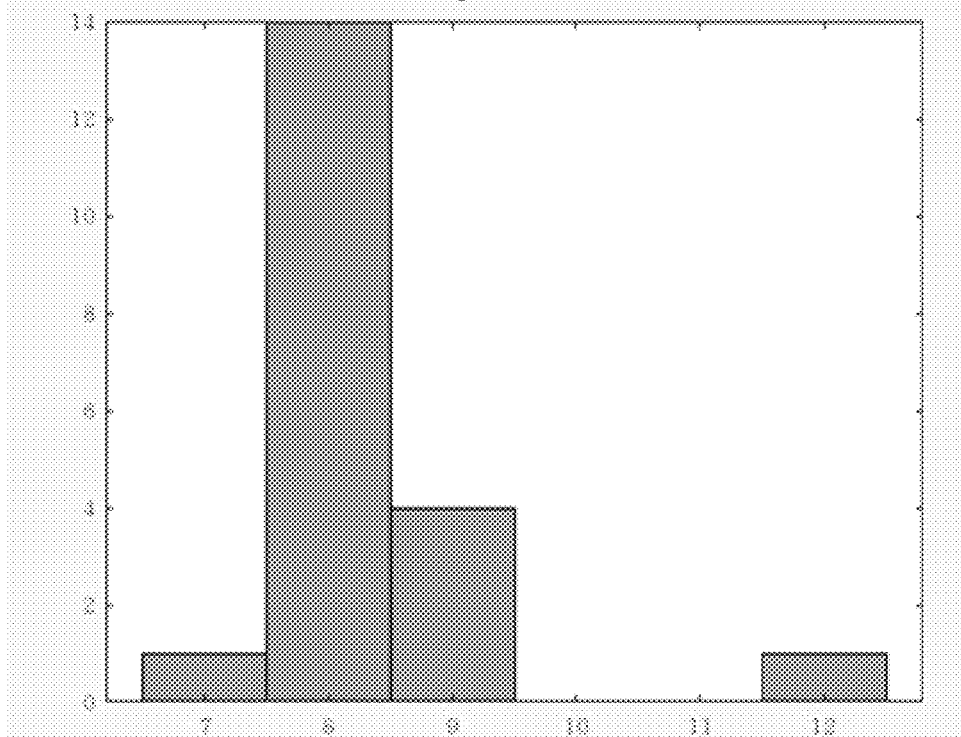
FIG. 13 is a beam data statistical diagram disclosed in an embodiment of the present disclosure.

Each row represents an array of planned angles. The length of the array is determined according to the maximum number of beams, and the number of beams for each plan is recorded in advance with a variable. First, the beam data is counted, obtaining the image shown in FIG. 13.

Figure 14:
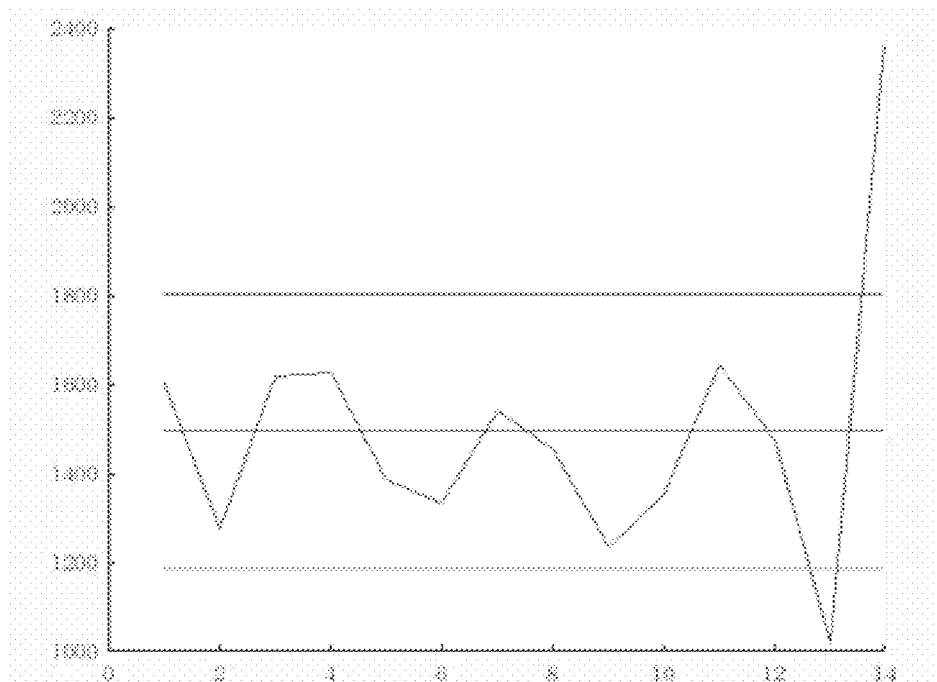
FIG. 14 is a beam data screening diagram disclosed in an embodiment of the present disclosure.

As can be known from the distribution of the number of beams, 8 beams are used for treatment mostly, with a frequency of 14. These 14 plans are used as screening plans, and the screening formula shall be applied, obtaining the results shown in FIG. 14; that is, the three horizontal lines from top to bottom respectively represent the mean value that is one time larger than the standard deviation, the mean value, and the mean value that is one time smaller than the standard deviation. It is considered that the cases within the range of one time the standard deviation are the cases where the beam angle is close, so two cases can be excluded, and the remaining 12 sets of planning cases can be used for training.

Figure 15:
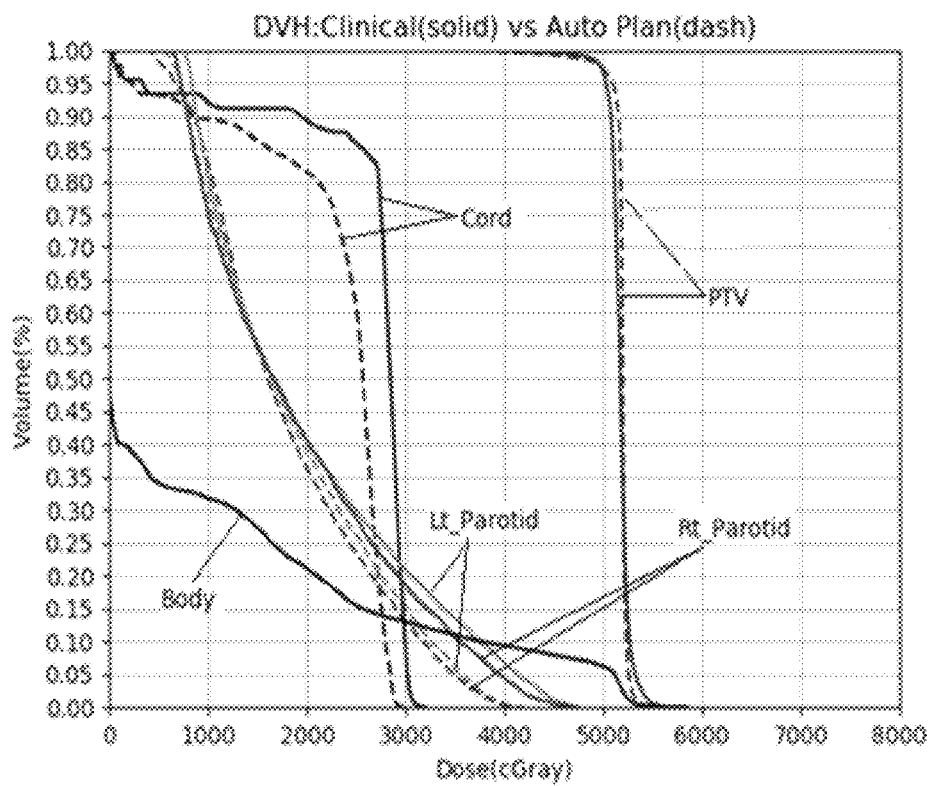
FIG. 15 is an effect diagram of using a GAN network for prediction according to an embodiment of the present disclosure.

Then, according to the automatic dose prediction model that considers the beam angle provided by the above embodiment, in the process of automatic dose prediction, case collection is performed through automatic evaluation, and the case screening is carried out using a unified standard template according to classification of the disease type (early and late onset, prescription dose, and cancerous location, etc.), and training is conducted upon CT, delineation, and dose together to generate a prediction model to perform dose prediction. The input of the prediction is CT and CT-based automatic delineation (RS), and the output result of the prediction is the slice dose corresponding to each CT slice image or the DVH generated thereby. Taking an effect diagram of using GAN network for prediction in a head and neck case as an example, as shown in FIG. 15, it can be seen that the prediction result in the PTV part is slightly better than the original result.

In the above-mentioned embodiment, preferably, said performing optimization processing using a reverse optimization algorithm based on dose distribution or DVH guidance, with reference to the radiation dose distribution result, to generate executable radiation therapy plans specifically includes: optimizing a flux weight map based on a flux map optimization algorithm; and then automatically generating an executable dynamic intensity modulated radiation therapy plan by a leaf sequence algorithm in combination with machine information of an accelerator; or,

|    | 1   | 2   | 3   | 4   | 5   | 6   | 7     | 8   | 9   | 10  | 11  | 12  |
|----|-----|-----|-----|-----|-----|-----|-------|-----|-----|-----|-----|-----|
| 1  | 15  | 100 | 115 | 120 | 155 | 298 | 303   | 330 | 340 | 0   | 0   | 0   |
| 2  | 295 | 300 | 330 | 75  | 105 | 110 | 120   | 140 | 0   | 0   | 0   | 0   |
| 3  | 150 | 115 | 110 | 100 | 20  | 340 | 330   | 300 | 298 | 0   | 0   | 0   |
| 4  | 295 | 300 | 330 | 330 | 100 | 105 | 117   | 140 | 0   | 0   | 0   | 0   |
| 5  | 0   | 110 | 115 | 145 | 300 | 305 | 330   | 0   | 0   | 0   | 0   | 0   |
| 6  | 295 | 300 | 330 | 0   | 95  | 105 | 112   | 145 | 0   | 0   | 0   | 0   |
| 7  | 297 | 300 | 330 | 340 | 15  | 110 | 120   | 160 | 0   | 0   | 0   | 0   |
| 8  | 300 | 305 | 330 | 105 | 120 | 125 | 130   | 145 | 0   | 0   | 0   | 0   |
| 9  | 308 | 315 | 330 | 345 | 0   | 15  | 105   | 117 | 158 | 0   | 0   | 0   |
| 10 | 215 | 245 | 250 | 255 | 350 | 30  | 60    | 63  | 0   | 0   | 0   | 0   |
| 11 | 145 | 119 | 105 | 100 | 20  | 300 | 303   | 335 | 0   | 0   | 0   | 0   |
| 12 | 165 | 111 | 101 | 5   | 0   | 330 | 316...| 298 | 0   | 0   | 0   | 0   |
| 13 | 0   | 10  | 100 | 105 | 110 | 115 | 120   | 300 | 305 | 310 | 320 | 330 |
| 14 | 155 | 113 | 110 | 105 | 10  | 300 | 305   | 330 | 0   | 0   | 0   | 0   |
| 15 | 155 | 110 | 105 | 10  | 300 | 305 | 308   | 330 | 0   | 0   | 0   | 0   |
| 16 | 0   | 0   | 104 | 120 | 165 | 302 | 308   | 340 | 0   | 0   | 0   | 0   |
| 17 | 155 | 117 | 113 | 105 | 10  | 300 | 305   | 330 | 0   | 0   | 0   | 0   |
| 18 | 302 | 305 | 330 | 352 | 10  | 100 | 105   | 120 | 155 | 0   | 0   | 0   |
| 19 | 10  | 100 | 115 | 123 | 155 | 303 | 305   | 330 | 0   | 0   | 0   | 0   |
| 20 | 302 | 320 | 325 | 345 | 0   | 0   | 113   | 118 | 0   | 0   | 0   | 0   |

Automatically generating an executable static intensity modulated radiation therapy plan based on a direct subfield optimization method; or, Automatically generating a volume intensity modulated radiation therapy plan or a rotational intensity modulated radiation therapy plant based on genetic algorithm or column generation algorithm; or, Forward radiation therapy plan; or, Stereotactic radiation therapy plan.

Specifically:

Automatic reverse planning is to use the above-mentioned predict dose distribution or DVH as the reference dose distribution or reference DVH, optimize a flux weight map by using a reverse optimization algorithm based on dose distribution or DVH guidance in combination with a voxel dose unit calculated by a specific dose calculation engine, and automatically obtain a final treatment plan by using a leaf sequence algorithm in combination with machine information of a specific accelerator; wherein the optimization algorithm can be implemented by a linear model or a nonlinear model.

The generated plan automatically calls the automatic plan evaluation-including the scores and total scores, which will be provided to doctors for approval;

Taking a linear model of an automatic optimization model as an example:

A plan optimization engine uses a series of linear objective functions to form a reverse plan optimization problem:

Setting a dose maximum objective function, a dose average objective function, and an equivalent uniformity objective function for each OAR;

The dose maximum objective function:

$$y^i = \max_{v \in \mathcal{O}^i}\{d_v\}, \forall i \in \mathcal{I}.$$

The dose average objective function:

$$z^i = \operatorname*{mean}_{v \in \mathcal{O}^i}\{d_v\}, \forall i \in \mathcal{I},$$

The equivalent uniformity objective function:

$$h^f = \operatorname*{mean}_{v \in \mathcal{O}^i}\{\max\{0, d_v - f\}\}, \forall f \in \mathcal{F}^i, \forall i \in \mathcal{I}.$$

Setting a dose maximum objective function for each PTV, and an objective function of deviation from the of prescription dose degree;

The dose maximum objective function:

$$y^t = \max_{v \in \mathcal{O}^t}\{d_v\}, \forall t \in \mathcal{T}.$$

The objective function of deviation from the of prescription dose degree:

$$l^t = \operatorname*{mean}_{v \in \mathcal{O}^t}\{\max\{0, \theta^t - d_v\}\}, \forall t \in \mathcal{T},$$

$$u^t = \operatorname*{mean}_{v \in \mathcal{O}^t}\{\max\{0, d_v - \theta^t\}\}, \forall t \in \mathcal{T}.$$

Setting a smooth constraint objective function of Fluence Map to ensure executability of the plan;

The smooth objective function:

$$m^k = \max_{r \in \mathcal{R}^k}\left\{\sum_{b \in \mathcal{B}^r}\max\{0, w_b - w_{b'}\}\right\}, \forall k \in \mathcal{K},$$

The entire reverse plan optimization problem can be linearly expressed as the following formula:

$$\operatorname*{minimize}_{z,y,x,l,u,m,g,w} \sum_{i \in \mathcal{I}}\left(\gamma^i z^i + \beta^i y^i + \sum_{f \in \mathcal{F}^i}\kappa^f \sum_{v \in \mathcal{O}^i} x_v^f\right) +$$

$$\sum_{t \in \mathcal{T}}(\beta^t y^t + \phi^t l^t + \psi^t u^t) + \sum_{k \in \mathcal{K}} m^k$$

$$\text{subject to } z^i \frac{1}{|\mathcal{O}^i|}\sum_{v \in \mathcal{O}^i}\sum_{k \in \mathcal{K}}\sum_{r \in \mathcal{R}^k}\sum_{b \in \mathcal{B}^r} D_{v,b} w_b, \forall_i \in \mathcal{I},$$

$$y^i \geq \sum_{k \in \mathcal{K}}\sum_{r \in \mathcal{R}^k}\sum_{b \in \mathcal{B}^r} D_{v,b} w_b, \forall v \in \mathcal{O}^i, \forall_i \in \mathcal{I},$$

...

...

...

Wherein $\gamma^i$ $\beta^i$ $\kappa^i$ $\beta^t$ $\phi^t$ $\varphi^t$ are weight parameters of each objective function, that is, the parameters that physicists need to adjust repeatedly. It happens that the reverse planning optimization model can optimize these parameters based on the dose distribution data predicted by an AI dose prediction model, that is, the AI model learns from historical cases how to design a plan. The above reverse plan optimization problem is expressed below in the form of a matrix:

$$\operatorname*{minimize}_{x} \alpha' C x + g' x$$

$$\text{subject to } Ax \geq b, x \geq 0.$$

α is a weight parameter vector
C is an objective function expression matrix
x is a decision variable
g is a smooth objective function expression matrix
A is a constraint factor matrix
b is a constraint boundary The following is the dual problem of the original reverse problem:

$$\operatorname*{maximize}_{p} b' p$$

-continued $$\text{subject to } C'\alpha + g \geq A'p.p \geq 0.$$

p is a dual variable of the constraints of the original problem

Accordingly, if it is intended to obtain α through optimization, the original problem could be turned into a form of optimizing the absolute dual gap:

$$\underset{\alpha,p}{\text{minimize}} \ \alpha'C\hat{x} + g'\hat{x} - b'p$$

$$\text{subject to } C'\alpha + g \geq A'p, \alpha \geq 0, p \geq 0.$$

C'x is value of each objective function, which can be learned by an AI dose prediction engine;

g $\hat{x}$ is a constant for a clinical plan, which, making no contribution to the optimization problem, can be discarded. The final problem becomes:

$$\underset{\alpha,p}{\text{minimize}} \ \alpha'C\hat{x} - b'p$$

$$\text{subject to } C'\alpha + g \geq A'p, \alpha \geq 0, p \geq 0.$$

Obviously, the final optimization model is a standard linear programming problem. The model can optimize the value of x, and then the value is substituted into the original reverse planning optimization model:

$$\underset{x}{\text{minimize}} \ \alpha'Cx + g'x$$

$$\text{subject to } Ax \geq b, x \geq 0.$$

α is known, and the above model relates to a standard linear programming problem, which can also optimize the x (Fluence map), and finally generates a high-quality plan.

Figure 16:
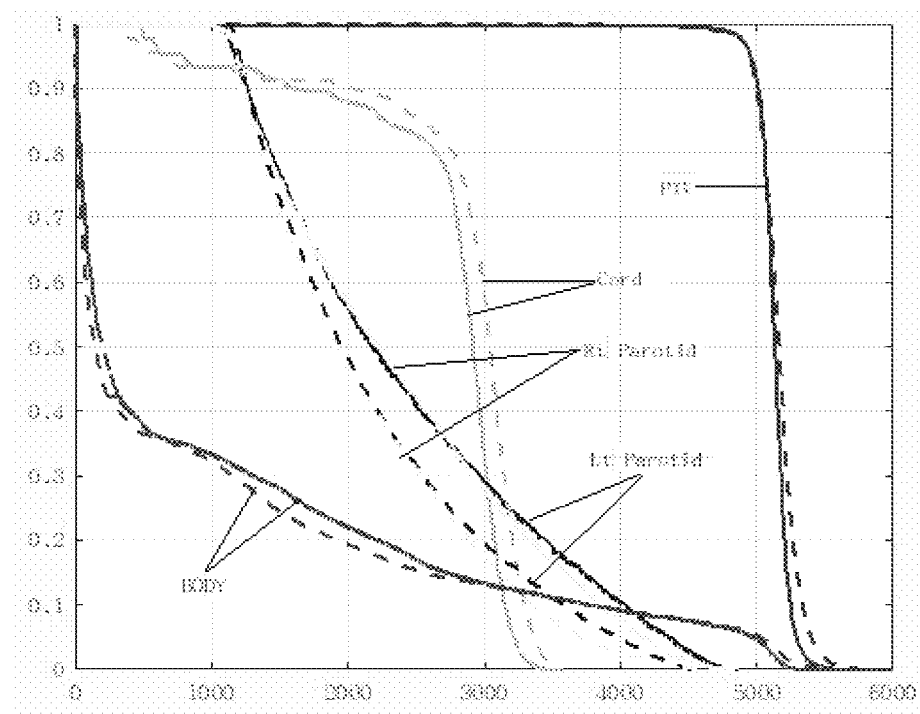
FIG. 16 is a diagram of DVH comparison results disclosed in an embodiment of the present disclosure.

In the present disclosure, using the head and neck case in the national standard YY/T0889 (consistent with the AAPM TG 119 example), algorithm test is conducted with respect to the automatic planning prototype proposed in the above embodiment. It can automatically optimize a plan that meets regulatory requirements without manual intervention. The total time consumption is about 5 minutes, and users only need to input prescription dose requirement and predicted three-dimensional dose data. The final DVH comparison result is shown in FIG. 16. The solid lines and the dashed lines respectively represent the artificially optimized DVH and the automatic reverse-optimized DVH, and the predicted DVH is used in the automatic optimization.

Figure 17:
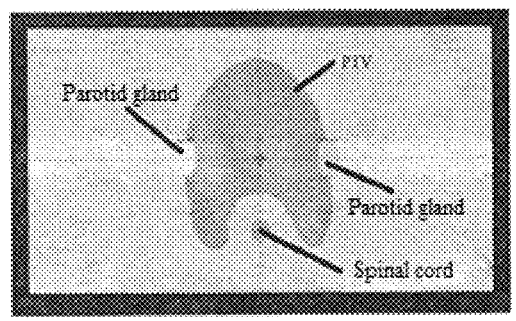
FIG. 17 is a cross-sectional view of a simulated head and neck tumor disclosed in an embodiment of the present disclosure

The constraints and target requirements of the examples in the national standard are shown in FIG. 17. It can be seen from FIG. 17 that the DVH result provided by the automatic plan is slightly worse than that of the manual PTV, but it is also a plan that meets the requirements. And the automatic plan only takes about 5 minutes, while the manual plan takes at least an hour.

Further, the method of automatic dose prediction in the present disclosure is:
  a) Case collection and automatic screening;
  b) Construction of an automatic dose prediction model considering beam angles;
  c) Artificial intelligence (AI) training of cases; and
  d) Automatic dose prediction of the cases.

The above automatic dose prediction steps can be replaced by automatic dose volume histogram (DVH) prediction:
  Method 1: DVH prediction based on machine learning:
    a) Case collection and screening;
    b) Construction of an automatic dose prediction model considering beam angle;
    c) Artificial intelligence (AI) training of cases; and
    d) DVH prediction of the cases.
  Method 2: DVH prediction based on statistical methods:
    a) Case collection and screening;
    b) DVH statistics of cases; and
    c) DVH prediction of the cases.
  Method 3: DVH prediction based on template
    a) Generation of an initial target constraint items using a preset template;
    b) Algorithm automatically adds constraint items and adjusts weights;
    c) The algorithm automatically adds auxiliary organs;
    d) DVH prediction of the cases.

In the above embodiment, preferably, the radiation therapy planning method further includes: scoring the generated executable radiation therapy plan through the combination of unified prescription standards and artificial intelligence to obtain a total score of plan evaluation; performing 2D or 3D Gamma analysis on the generated executable radiation therapy plan using Monte Carlo three-dimensional dose verification technology, to obtain a pass rate of the Gamma analysis; automatically generating a radiation therapy plan report based on the executable radiation therapy plan, the total score of plan evaluation and the pass rate of the Gamma analysis; a doctor reviews the radiation therapy plan report.

Specifically, with regard to scoring the generated executable radiation therapy plan through the combination of unified prescription standards and artificial intelligence (Artificial Intelligence, AI for short) to obtain a total score of plan evaluation,
  1. Standardization of Naming of Specific Disease Type
  In order to ensure that the lineated structure aliases can be automatically extracted as uniform names when training preprocessed data, a mapping dictionary list of standard names and aliases needs to be developed, as shown in FIG. 18;
  2. Automatic Plan Evaluation
  The premise of automatic planning is to have an excellent planning database. Therefore, an algorithm and tool for automatically screening excellent plans is needed. This tool can be used for plan screening, and can also be used for scoring after automatic plan generation.
  Evaluation software is positioned as a multi-functional information and data management application, used to help doctors and physicists improve and enhance the standardization of radiation therapy plans, and used to score and screen existing planning cases to select cases with higher and lower scores respectively for machine learning training and prediction testing. The input of the application program is the DICOM data exported by the treatment planning system (TPS), including two parts: RS and RD. The output is the scoring result. The scoring template required by the evaluation software is formulated by each hospital's unified rules, and different templates can be developed for different disease types or even more specific classifications. International standards and the hospital's own internal standards can be referred to in the formulation process.

In the present disclosure, in order to make an equal comparison between all plans, the dose prediction model uses the PTV average dose of 5000 cGy to standardize the plans. Normalization of the PTV average dose establishes a unified data set, which is more conducive to training the model, and the normalized plan brings about greater clinical relevance and evaluation value. Production of the scoring template is based on summary and exchange of information from RTOG-1005, physicists and radiologists with more than 5 years of work experience. The scoring template contains the following items: PTV's V48, V50, V53, V55, DMAX, D2, D98, HI, CI; heart's V10, DMEAN; left lung's V4, V5, DMEAN; right lung's V4, V5, V8, V10, V20, V30, DMEAN and DMAX of the spinal cord. The data is scored by setting the upper and lower limits of volume and dose. The closer the upper limit is, the higher the score will be, and no score will be obtained without exceeding the lower limit. At the same time, different weights are assigned to attributes to make them meeting doctor's prescription requirements and clinical needs in a better way. The purpose of making a scoring template is as follows: 1. selecting wrong data by formulating a scoring template to prevent from affecting accuracy of the model since there may be left and right breast errors, disease errors and other things occurring in the process of data selection; 2. normalized data is conducive to accuracy of the training model.

Specifically, with regard to performing 2D or 3D Gamma analysis on the generated executable radiation therapy plan using Monte Carlo three-dimensional dose verification technology, to obtain a pass rate of the Gamma analysis, the generated plan automatically uses the 3D Gamma analysis based on Monte Carlo QA; and giving the pass rate of Gamma analysis is for providing reference for doctors to finally approve the plan, pushing accurate radiation therapy forward.

With regard to automatically generating a radiation therapy plan report based on the executable radiation therapy plan, the total score of plan evaluation and the pass rate of the Gamma analysis, and a doctor reviewing the radiation therapy plan report:

Review report has a summary and detailed contents. The summary describes the pass rate of the 3D Gamma analysis of QA, the total score of the plan evaluation, and the summary of the plan to be executed; the detailed introduction of each content is convenient for the doctor to carefully review the automatic plan. If the approval is passed, it will be published to the medical accelerator for execution; if the approval is not passed, manual intervention is allowed to modify the plan manually.

As shown in FIG. 19, in the above embodiment, preferably, with respect to the radiation therapy dose distribution result, it further includes: entering a dose editing mode when a dose editing trigger instruction is received; a section graph of a spatial dose model on a current radiation therapy image section moves with a trajectory of a control cursor, where position of the control cursor is a center of the spatial dose model, and the trajectory of the control cursor corresponds to a moving trajectory of an action control device; monitoring action events of the action control device, and adjusting a dose at a center point of the spatial dose model according to a preset control command corresponding to the action events; calculating doses at other points in the spatial dose model by interpolation on basis of the dose at the center point of the spatial dose model; saving and updating dose data at each point in the spatial dose model, without amendment to dose data in the area outside the spatial dose model.

In this embodiment, users are able to obtain their expected dose distribution visually and directly by directly using an editing tool to edit radiation therapy dose, which is faster and more visual than the method of indirectly adjusting parameters to influence the dose distribution and greatly improves efficiency of the planning design.

In the above-mentioned embodiment, preferably, said adjusting a dose at a center point of the spatial dose model according to a preset control command corresponding to the action events specifically includes: when the action events are monitored, a dose adjustment indication label is floating displayed; when it is monitored that the action control device is triggered with a first action event when the control cursor is located in an area of the dose adjustment indication label, a dose value corresponding to the position where the control cursor is located is taken as the dose at the center point of the spatial dose model; when it is monitored that the action control device is triggered with a second action event when the control cursor is located on an indication slide on the dose adjustment indication label, a dose value corresponding to position of the control cursor when clicking the second action event is released is used as the dose at the center point of the spatial dose model; when it is monitored that the action control device is triggered with a third action event when the control cursor is in the current section graph, action parameters of the third action event are used for adjusting the dose at the center point of the spatial dose model; when it is monitored that the action control device is triggered with the third action event when the control cursor is not in the current section graph, a radiation therapy image is turned over with the action parameters of the third action event, and when it is removed from the area of the section graph, the dose adjusted by the third action event is saved.

In the above-mentioned embodiment, preferably, the radiation therapy planning method further includes: monitoring the action event of the action control device, and according to the preset control command corresponding to the action event, the radiation therapy image where the spatial dose model is located can also be turned over, and size of the spatial dose model can be adjusted; when it is monitored that the action control device is triggered with a fourth action event, the size of the spatial dose model is adjusted according to action parameters of the fourth action event.

The spatial dose model is a sphere, cube, cuboid or ellipsoid, and the action control device is a mouse or other human-computer interaction control device. If a mouse is used as the action control device, the first action event of the action control device could be clicking of left key of the mouse, the second action event could be moving the mouse with the left key being clicked and keeping the clicked state, the third action event could be scrolling a wheel of the mouse, and the fourth action event could be moving the mouse with the right key being clicked and keeping the clicked state.

Preferably, doses at the center point of the dose sphere and other points in the spatial model dose model are updated and saved to the database after their calculation, and they are updated and displayed in a front end in a form of statistical data of DVH, isodose line and/or dose volume histogram.

Figure 20:
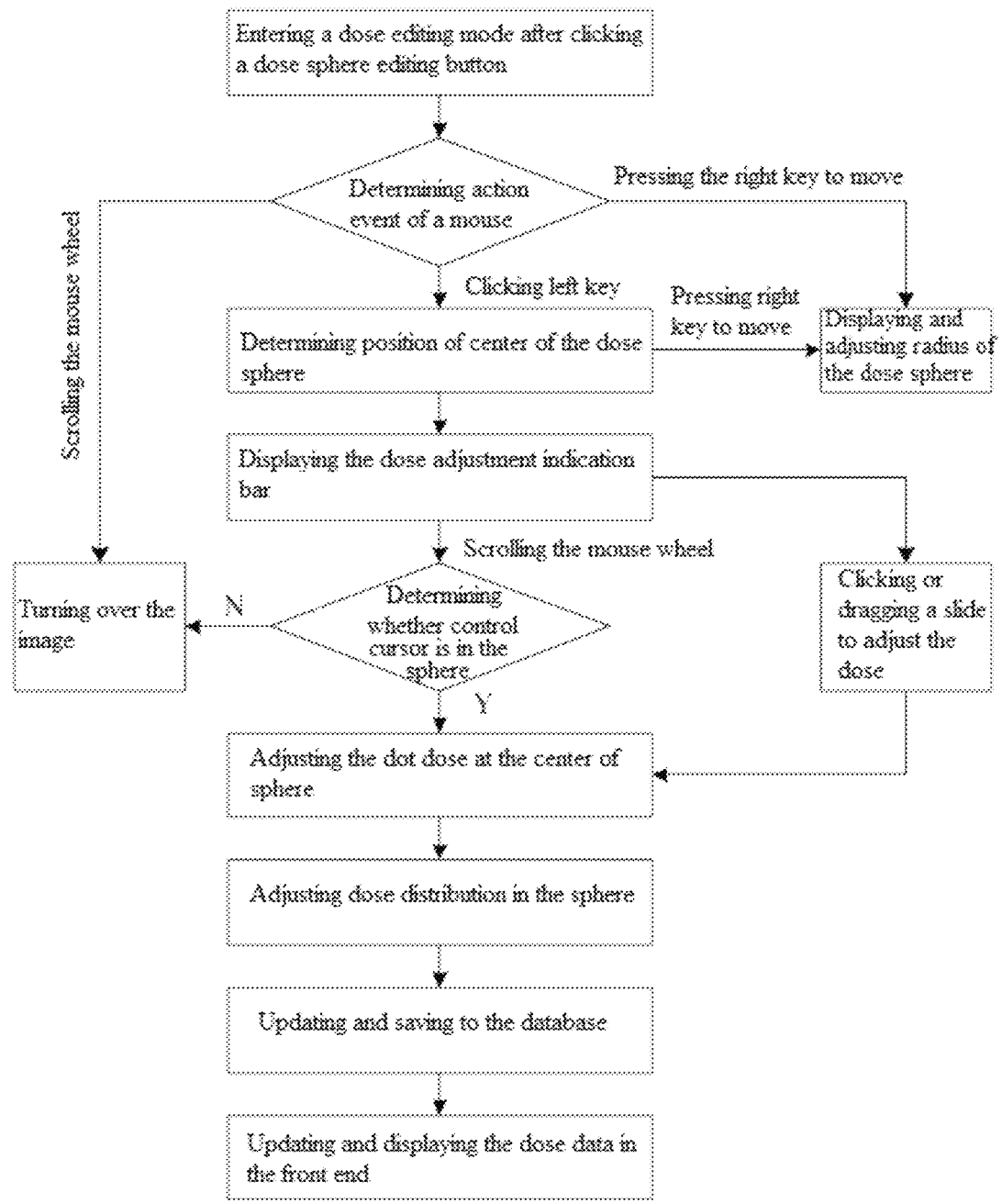
FIG. 20 is a schematic block diagram of the flow of the dose editing method disclosed in an embodiment of the present disclosure.

As shown in FIG. 20, specifically, taking the mouse as the action control device and the spatial dose model of the sphere as an example, the method of dose editing in a radiation therapy planning system is described in detail, and the method of dose editing in the radiation therapy planning system specifically includes:

1. Entering a dose editing mode after clicking a dose sphere editing button and receiving a dose editing trigger command;
2. A tangent circle of the dose sphere on the current radiation therapy image section moves with the trajectory of the control cursor, wherein the control cursor is positioned at the center of the dose sphere, and the trajectory of the control cursor corresponds to the moving trajectory of the mouse;
3. Monitoring action events of the mouse, turning the radiation therapy image over when the mouse wheel is scrolling, and adjusting a radius of the dose sphere when the right key of the mouse is clicked and kept in the clicked state;
4. Taking a current position of the control cursor as the position of the center of the dose sphere when the left key of the mouse is clicked, and meanwhile displaying a dose adjustment indicator bar at the same time, whereby position of a dose slide is a dot dose current at the center of the sphere;
5. There are three ways of dose editing, and different mouse events complete different functions:
    1) When the control cursor is in the tangent circle, the dot dose at the center of the sphere can be increased and reduced when the mouse wheel is scrolled up and down. The mouse wheel can be scrolled up by n steps, with a scroll step length of (Du-D0)/n, and the mouse wheel can be scrolled down by m steps, with a scroll step length of (D0-Dl)/m, where Dl is the lower limit of the adjustable dose, Du is the upper limit of the adjustable dose, and D0 is the dot dose at the center of the dose sphere when the left key of the mouse is clicked, and n and m are constants;
    2) Clicking and dragging the slide on the dose adjustment indicator bar with the left key of the mouse. After the mouse is released, the dose at the center of the sphere is adjusted to the dose value at the position of the slide;
    3) When the dose adjustment indicator bar is clicked with the left key of the mouse, the slide is moved to the clicked position, and the dose at the center of the sphere is adjusted to the dose value at the position of the slide;
6. Re-adjustment of the dose distribution in the dose sphere: after the dose at the center of the dose sphere is edited and determined, the dose at each point of the space within the dose sphere is obtained by interpolation algorithm from the dose at the edge and center of the dose sphere;
7. After the position of the dose sphere is determined, the radius of the dose sphere can still be displayed and adjusted by pressing the right key of the mouse to move;
8. When controlling the cursor to move out of the tangent circle, scrolling the mouse wheel can realize the image layer turning function;
9. Save and update of the dose: after the dose distribution in the sphere is adjusted, the edited dose will be automatically saved to the database;
10. Updating and displaying dose data in the front end, including dose volume histogram, isodose line, DVH statistics, etc.

In the above embodiment, preferably, the interpolation algorithm includes linear interpolation, bilinear interpolation, cubic interpolation, bicubic interpolation, nearest neighbor interpolation, cubic convolution interpolation algorithm, natural neighbor interpolation, triangulation/linear interpolation, Sebeide method, radial basis function method, multiple regression method, minimum curvature method, kriging method and distance reciprocal multiplication method.

Preferably, after the position of the center point of the dose sphere is determined, the radius of the dose sphere can also be adjusted when the right key of the mouse is clicked and kept moving. In addition to the direct and visual way to edit the dose, a dose in some volume of interest can be modified by adjusting the integral DVH curve or adjusting the differential DVH curve; modifying dose distribution by editing the isodose line; modifying the dose distribution by such methods as using a brush of a dose cloud; modifying the dose distribution in the three-dimensional view of the dose, and editing the dose.

In the foregoing embodiment, preferably, the upper limit Dl and the lower limit Du of the dose adjustment at the center of the spatial dose model are respectively:

$$Dl = \begin{cases} D0 - n*R, & D0 - n*R \geq 0 \\ 0, & D0 - n*R < 0 \end{cases}$$

$$Du = \begin{cases} D0 + n*R, & D0 + n*R \leq Dmax \\ Dmax, & D0 + n*R > Dmax \end{cases}$$

wherein, Dl is the lower limit of the adjustable dose, Du is the upper limit of the adjustable dose, D0 is the dot dose at the center of the spatial dose model when the action event of the action control device is triggered, R is the characteristic parameter of the spatial dose model, and Dmax is the global maximum dose value of the dose data, n is a constant.

The present disclosure also provides a standardized artificial intelligence automatic radiation therapy planning system, which is used to realize the standardized artificial intelligence automatic radiation therapy planning method according to any one of the above embodiments.

The present disclosure also provides a computing device, including:
    one or more processor;
    a memory; and
    one or more programs, wherein said one or more programs are stored in the memory and configured to be executed by said one or more processor, and the one or more programs include instructions for realizing the aforementioned standardized artificial intelligence automatic radiation therapy planning method.

The present disclosure also provides a computer-readable storage medium storing one or more programs, the one or more programs including instructions, which are adapted to be loaded by a memory and execute the aforementioned standardized artificial intelligence automatic radiation therapy planning method.

The above are only preferred embodiments of the present disclosure, which are not used to limit the present disclosure. For those skilled in the art, the present disclosure can have various modifications and changes. Any modification, equivalent replacement, improvement, etc., made within the spirit and principle of the present disclosure should be included in the protection scope of the present disclosure.

What is claimed is:

1. A standardized artificial intelligence automatic radiation therapy planning method, characterized in comprising:
    acquiring a medical image;
    automatically delineating an ROI area of the medical image to acquire a geometric anatomical structure;

determining a prescription according to disease type information corresponding to the medical image, the geometric anatomical structure, and a preset disease-prescription template library;

determining a radiation angle of radiation therapy according to the disease type information, the geometric anatomical structure and the prescription;

inputting the medical image, the geometric anatomical structure, the disease type information, the prescription and the radiation angle of radiation therapy into a dose prediction model to obtain a radiation dose distribution result;

performing optimization processing using a reverse optimization algorithm based on dose distribution or DVH guidance, with reference to the radiation dose distribution result, to generate executable radiation therapy plans; and the executable radiation therapy plans include forward radiation therapy plans, stereotactic radiation therapy plans and intensity-modulated radiation therapy plans, wherein the intensity-modulated radiation therapy plans include dynamic intensity-modulated radiation therapy plans, static intensity-modulated radiation therapy plans, volume-intensity-modulated radiation therapy plans, and rotational intensity-modulated radiation therapy plans.

2. The standardized artificial intelligence automatic radiation therapy planning method according to claim 1, wherein the method further comprises scoring the generated executable radiation therapy plan through combination of unified prescription standards and artificial intelligence to obtain a total score of plan evaluation;

performing 2D or 3D Gamma analysis on the generated executable radiation therapy plan using Monte Carlo three-dimensional dose verification technology, to obtain a pass rate of the Gamma analysis;

automatically generating a radiation therapy plan report based on the executable radiation therapy plan, the total score of plan evaluation and the pass rate of the Gamma analysis; and a doctor reviews the radiation therapy plan report.

3. A standardized artificial intelligence automatic radiation therapy planning system, characterized in that the radiation therapy planning system is used for implementing the standardized artificial intelligence automatic radiation therapy planning method according to claim 2.

4. The standardized artificial intelligence automatic radiation therapy planning method according to claim 1, wherein, with respect to the radiation dose distribution result, the method further comprises:

entering a dose editing mode when a dose editing trigger instruction is received;

a section graph of a spatial dose model on a current radiation therapy image section moves with a trajectory of a control cursor, wherein position of the control cursor is a center of the spatial dose model, and the trajectory of the control cursor corresponds to a moving trajectory of an action control device;

monitoring action events of the action control device, and adjusting a dose at a center of the spatial dose model according to a preset control command corresponding to the action events;

calculating doses at other points in the spatial dose model by interpolation on basis of the dose at the center of the spatial dose model; and saving and updating dose data at each point in the spatial dose model, without amendment to dose data in an area outside the spatial dose model.

5. The standardized artificial intelligence automatic radiation therapy planning method according to claim 3, wherein said adjusting a dose at a center point of the spatial dose model according to a preset control command corresponding to the action events specifically comprises:

when the action events are monitored, a dose adjustment indication label is floating displayed;

when it is monitored that the action control device is triggered with a first action event when the control cursor is located in an area of the dose adjustment indication label, a dose value corresponding to the position where the control cursor is located is taken as the dose at the center point of the spatial dose model;

when it is monitored that the action control device is triggered with a second action event when the control cursor is located on an indication slide on the dose adjustment indication label, a dose value corresponding to position of the control cursor when clicking the second action event is released is used as the dose at the center point of the spatial dose model;

when it is monitored that the action control device is triggered with a third action event when the control cursor is in the current section graph, action parameters of the third action event are used for adjusting the dose at the center point of the spatial dose model; and when it is monitored that the action control device is triggered with the third action event when the control cursor is not in the current section graph, a radiation therapy image is turned over with the action parameters of the third action event, and when it is removed from the area of the section graph, the dose adjusted by the third action event is saved.

6. The standardized artificial intelligence automatic radiation therapy planning method according to claim 5, wherein upper limit Dl and lower limit Du of the dose adjustment at the center point of the spatial dose model are respectively:

$$Dl = \begin{cases} D0 - n*R, & D0 - n*R \geq 0 \\ 0, & D0 - n*R < 0 \end{cases}$$

$$Du = \begin{cases} D0 + n*R, & D0 + n*R \leq Dmax \\ Dmax, & D0 + n*R > Dmax \end{cases}$$

wherein, Dl is a lower limit of the adjustable dose, Du is an upper limit of the adjustable dose, D0 is the dot dose at the center of the spatial dose model when the action event of the action control device is triggered, R is the characteristic parameter of the spatial dose model, and Dmax is the global maximum dose value of the dose data, n is a constant.

7. A standardized artificial intelligence automatic radiation therapy planning system, characterized in that the radiation therapy planning system is used for implementing the standardized artificial intelligence automatic radiation therapy planning method according to claim 6.

8. A standardized artificial intelligence automatic radiation therapy planning system, characterized in that the radiation therapy planning system is used for implementing the standardized artificial intelligence automatic radiation therapy planning method according to claim 5.

9. The standardized artificial intelligence automatic radiation therapy planning method according to claim 4, wherein the method further comprises:

monitoring the action event of the action control device, and according to the preset control command corresponding to the action event, the radiation therapy image where the spatial dose model is located can also be turned over, and the size of the spatial dose model can be adjusted;

when it is monitored that a fourth action event is triggered by the action control device, the size of the spatial dose model is adjusted according to the action parameters of the fourth action event.

10. A standardized artificial intelligence automatic radiation therapy planning system, characterized in that the radiation therapy planning system is used for implementing the standardized artificial intelligence automatic radiation therapy planning method according to claim 9.

11. A standardized artificial intelligence automatic radiation therapy planning system, characterized in that the radiation therapy planning system is used for implementing the standardized artificial intelligence automatic radiation therapy planning method according to claim 4.

12. The standardized artificial intelligence automatic radiation therapy planning method according to claim 4, wherein upper limit Dl and lower limit Du of the dose adjustment at the center point of the spatial dose model are respectively:

$$Dl = \begin{cases} D0 - n*R, & D0 - n*R \geq 0 \\ 0, & D0 - n*R < 0 \end{cases}$$

$$Du = \begin{cases} D0 + n*R, & D0 + n*R \leq Dmax \\ Dmax, & D0 + n*R > Dmax \end{cases}$$

wherein, Dl is a lower limit of the adjustable dose, Du is an upper limit of the adjustable dose, D0 is the dot dose at the center of the spatial dose model when the action event of the action control device is triggered, R is the characteristic parameter of the spatial dose model, and Dmax is the global maximum dose value of the dose data, n is a constant.

13. A standardized artificial intelligence automatic radiation therapy planning system, characterized in that the radiation therapy planning system is used for implementing the standardized artificial intelligence automatic radiation therapy planning method according to claim 5.

14. The standardized artificial intelligence automatic radiation therapy planning method according to claim 1, wherein said automatically delineating an ROI area of the medical image to acquire a geometric anatomical structure particularly comprises:

automatic identification and automatic delineation of normal organs: automatically identifying and delineating various normal organs of human body based on machine learning;

automatic identification and delineation of tumor site: delineating tumors in reverse if the whole body organs are able to be delineated; after delineation of organs at risk is completed, remaining part will be the tumor site; and the remaining part is automatically delineated using relationship between PTV expansion and GTV expansion acquired by machine learning;

said determining a radiation angle of radiation therapy according to the disease type information, the geometric anatomical structure and the prescription specifically comprises:

performing machine learning on the disease type information, the geometric anatomical structure and the prescription of historical cases, determining a radiation angle prediction model, and inputting the disease type information, the geometric anatomical structure and the prescription of a current case into the radiation angle prediction model to obtain a predicted radiation angle as the radiation angle of radiation therapy;

marking an organ weight of a planned target volume according to disease type, calculating a cumulative value of organ weights at all angles in a ray direction, merging adjacent angles that meet a preset weight threshold, and using the angles that meet the weight threshold as the radiation angle of radiation therapy; or determining regions of interest, selecting at least one planned target volume and one organ at risk, and performing full-angle radiation projection for each region of interest;

calculating a minimum bounding rectangle over the planned target volume at each angle of each segmented angle, and calculating an intersection between a minimum bounding rectangle of a certain organ at risk at the angle and the corresponding minimum bounding rectangle to obtain an intersection area; summing intersection areas of all segmented angles, taking the smallest sum as an objective function, and using a nonlinear integer optimization algorithm for solution to obtain an optimal segment index and an optimal angle index to serve as the radiation angle of radiation therapy.

15. A standardized artificial intelligence automatic radiation therapy planning system, characterized in that the radiation therapy planning system is used for implementing the standardized artificial intelligence automatic radiation therapy planning method according to claim 14.

16. The standardized artificial intelligence automatic radiation therapy planning method according to claim 1, wherein a method for constructing the dose prediction model comprises:

establishing a data set with a normalized PTV average dose, and formulating a scoring template based on the data set;

carrying out standardized naming for the region of interest;

dividing a 3D medical image into 2D slices as a training set and a test set;

reading out a beam angle of a 3D planned target volume data of the training set, and projecting the beam angle on the planned target volume to obtain a network weigh, and using a dose calculation algorithm to perform calculation on the network weight to obtain a beam channel;

constructing a Pix2pix dose prediction model using a U-net network or a V-net network as a generator, and a Markov discriminator as a discriminator;

using the 2D slice image as input of the generator, using predict dose and raw dose outputted by the generator as input of the discriminator, and outputting a discrimination result by the discriminator; and inputting all 2D slices of the training set into the Pix2pix dose prediction model for training.

17. A standardized artificial intelligence automatic radiation therapy planning system, characterized in that the radiation therapy planning system is used for implementing the standardized artificial intelligence automatic radiation therapy planning method according to claim 16.

18. The standardized artificial intelligence automatic radiation therapy planning method according to claim 1, wherein said performing optimization processing using a reverse optimization algorithm based on dose distribution or DVH guidance, with reference to the radiation dose distribution result, to generate executable radiation therapy plans specifically comprises:

optimizing a flux weight map based on a flux map optimization algorithm; and then automatically generating an executable dynamic intensity modulated radiation therapy plan by a leaf sequence algorithm in combination with machine information of an accelerator; or, automatically generating an executable static intensity modulated radiation therapy plan based on a direct subfield optimization method; or, automatically generating a volume intensity modulated radiation therapy plan or a rotational intensity modulated radiation therapy plant based on genetic algorithm or column generation algorithm; or, a forward radiation therapy plan; or, a stereotactic radiation therapy plan.

19. A standardized artificial intelligence automatic radiation therapy planning system, characterized in that the radiation therapy planning system is used for implementing the standardized artificial intelligence automatic radiation therapy planning method according to claim 18.

20. A standardized artificial intelligence automatic radiation therapy planning system, characterized in that the radiation therapy planning system is used for implementing the standardized artificial intelligence automatic radiation therapy planning method according to claim 1.

\* \* \* \* \*